US012654309B2

(12) United States Patent
Kose et al.

(10) Patent No.: US 12,654,309 B2
(45) Date of Patent: Jun. 16, 2026

(54) CONTINUUM ROBOT CONTROL SYSTEM AND CONTINUUM ROBOT CONTROL METHOD

(71) Applicant: CANON KABUSHIKI KAISHA, Tokyo (JP)

(72) Inventors: Hidekazu Kose, Tokyo (JP); Kosuke Fujimoto, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 28 days.

(21) Appl. No.: 18/785,706

(22) Filed: Jul. 26, 2024

(65) Prior Publication Data

US 2024/0383129 A1     Nov. 21, 2024

Related U.S. Application Data

(63) Continuation of application No. PCT/JP2022/048453, filed on Dec. 28, 2022.

(30) Foreign Application Priority Data

Jan. 28, 2022     (JP) ................................. 2022-012132

(51) Int. Cl.
B25J 9/10          (2006.01)
A61B 1/005        (2006.01)
(Continued)

(52) U.S. Cl.
CPC .............. B25J 9/104 (2013.01); A61B 1/005 (2013.01); A61B 10/04 (2013.01); B25J 9/1664 (2013.01);
(Continued)

(58) Field of Classification Search
CPC ......... B25J 9/104; B25J 9/1664; A61B 1/005; A61B 10/04; A61B 2010/0208;
(Continued)

(56) References Cited

U.S. PATENT DOCUMENTS

| | | | |
|---|---|---|---|
| 12,446,762 B2 * | 10/2025 | Yoshimura | ........... A61B 1/0052 |
| 2013/0041392 A1 * | 2/2013 | Edwards | ............ A61B 17/3207 |
| | | | 606/1 |

(Continued)

FOREIGN PATENT DOCUMENTS

| | | |
|---|---|---|
| CN | 110811702 A | 2/2020 |
| JP | 2005137527 A | 6/2005 |

(Continued)

OTHER PUBLICATIONS

International Search Report and Written Opinion for PCT/JP2022/048453, mailed Mar. 20, 2023, originally published in Japanese, and an English translation of International Search Report and Machine Translation into English of Written Opinion obtained from WIPO using WIPO Translate are included herewith.

*Primary Examiner* — Sohana Tanju Khayer

(74) *Attorney, Agent, or Firm* — CANON U.S.A., INC. IP DIVISION

(57) ABSTRACT

When a plurality of tools that are different are inserted into and extracted from a tool channel after a bending portion of a continuum robot has been inserted to an inside of a test body, a control device acquires, for each of the plurality of tools, a maximum value of bending angle at which the tool is capable of passing through a tool channel, sets a smallest of a plurality of the acquired maximum values of bending angle as a maximum bending angle, and controls a driving unit so that the bending portion bends within a range of the set maximum bending angle.

7 Claims, 15 Drawing Sheets

(51) Int. Cl.

| | | |
|---|---|---|
| *A61B 10/04* | (2006.01) | |
| *B25J 9/16* | (2006.01) | |
| *A61B 10/02* | (2006.01) | |

(52) U.S. Cl.
CPC ................ *A61B 2010/0208* (2013.01); *A61B 2010/0216* (2013.01); *A61B 2010/045* (2013.01)

(58) Field of Classification Search
CPC ...... A61B 2010/0216; A61B 2010/045; A61B 1/018; G02B 23/24
See application file for complete search history.

(56) References Cited

U.S. PATENT DOCUMENTS

| | | | | |
|---|---|---|---|---|
| 2014/0039259 | A1* | 2/2014 | Okaniwa | A61B 1/005 |
| | | | | 600/139 |
| 2016/0213227 | A1* | 7/2016 | Osaki | G02B 23/2476 |
| 2017/0143426 | A1* | 5/2017 | Isaacs | A61B 34/20 |
| 2017/0235341 | A1* | 8/2017 | Huitema | G04G 17/08 |
| | | | | 361/679.03 |

| | | | | |
|---|---|---|---|---|
| 2019/0321171 | A1* | 10/2019 | Morriss | A61F 2/2436 |
| 2020/0121167 | A1* | 4/2020 | Araki | G02B 23/24 |
| 2020/0129239 | A1* | 4/2020 | Bianchi | A61M 25/0105 |
| 2020/0218336 | A1* | 7/2020 | Chang | G06F 3/011 |
| 2020/0352422 | A1* | 11/2020 | Dejima | A61B 17/29 |
| 2020/0375682 | A1 | 12/2020 | Kincaid et al. | |
| 2021/0106317 | A1* | 4/2021 | Fisher | A61B 10/0266 |
| 2021/0121250 | A1* | 4/2021 | Uesugi | G02B 23/24 |
| 2021/0378648 | A1* | 12/2021 | Thissen | A61B 17/29 |
| 2022/0304554 | A1* | 9/2022 | Kawamoto | A61B 1/018 |
| 2022/0338715 | A1* | 10/2022 | Yoshimura | A61B 1/00006 |
| 2023/0110623 | A1* | 4/2023 | Ogundare | B65H 75/4489 |
| | | | | 166/381 |
| 2023/0277204 | A1* | 9/2023 | Ueda | A61B 17/2909 |
| | | | | 600/104 |
| 2024/0024047 | A1* | 1/2024 | Gerboni | A61B 90/37 |
| 2024/0277216 | A1* | 8/2024 | Keshtgar | A61B 1/008 |

FOREIGN PATENT DOCUMENTS

| | | |
|---|---|---|
| JP | 2010082435 A | 4/2010 |
| WO | 2020243285 A1 | 12/2020 |

* cited by examiner

CONTINUUM ROBOT CONTROL SYSTEM AND CONTINUUM ROBOT CONTROL METHOD

CROSS-REFERENCE TO RELATED APPLICATIONS

This application is a Continuation of International Patent Application No. PCT/JP2022/048453, filed Dec. 28, 2022, which claims the benefit of Japanese Patent Application No. 2022-012132, filed Jan. 28, 2022, both of which are hereby incorporated by reference herein in their entireties.

TECHNICAL FIELD

The present invention relates to: a continuum robot control system that controls a continuum robot including a tool channel that is a tubular path extending through the inside of a bending portion and through which a tool is to be inserted and extracted; and a continuum robot control method.

BACKGROUND ART

In recent years, minimally invasive medical treatment, for reducing burden on a test subject such as a patient and improving QOL after treatment/test, has been attracting attention. A representative example of minimally invasive medical treatment is surgery/test using an endoscope. For example, laparoscopic surgery, with which it is possible to make a surgical wound smaller than that of existing abdominal surgeries, has merits in that not only hospitalization period after surgery can be shortened but also appearance is good.

A flexible endoscope is known as an endoscope used for minimally invasive medical treatment. Since an insertion portion of the flexible endoscope that is inserted to the inside of a test subject is constituted by a bendable member, even for an organ that bends, such as an esophagus, a large intestine, or a lung, it is possible to insert the insertion portion to the inside of a test subject without pressing a tissue and to reduce burden on the test subject. Moreover, it is expected that burden on a test subject can be further reduced by driving the insertion portion of the flexible endoscope by using an actuator and automatically controlling the posture of the insertion portion along a path inside of the test subject. Some flexible endoscopes include a tool channel that allows tools, including surgical tools such as a tool for biopsy or a tool for a treatment, to be inserted therethrough. By using such an endoscope, it is possible not only to observe an affected area deep inside the body of a test subject but also to sample a tissue and to perform treatment. For these reasons, research and development of a mechanism of a continuum robot that is usable as a flexible endoscope and a method of controlling the continuum robot have been actively carried out.

It is desirable that a bending portion, which is an insertion portion of the continuum robot and is bendable by a driving portion such as an actuator, have a small diameter. This is because, when the bending portion, which is the insertion portion, has a small diameter, the bending portion can reach a deep part inside of the body of a test subject without pressing a lumen. In addition, when the bending portion, which is the insertion portion, has a smaller diameter, it is possible to diagnose or treat a larger area, because the bending portion can reach a deep part of an organ, such as a lung, in which the diameter of a lumen decreases toward the periphery.

PTL 1 describes an example of a flexible endoscope having an insertion portion whose diameter can be reduced. In contrast to existing flexible endoscopes, in which an imaging device for observing a lumen is incorporated in an insertion portion, the flexible endoscope described in PTL 1 is used by inserting an imaging tool from a tool channel only when needed for observation. With the flexible endoscope described in PTL 1, when an affected area is to be treated or a tissue is to be sampled from the affected area, the imaging tool is extracted from the tool channel and a surgical tool is inserted instead, and, subsequently, the surgical tool is extracted and the imaging tool is inserted again when the affected area is to be observed again. Thus, it is possible to reduce the diameter of the insertion portion by the amount of space needed to set the imaging device in existing flexible endoscopes.

CITATION LIST

Patent Literature

PTL 1 Japanese Patent Laid-Open No. 2010-82435

However, a high-rigidity member is used as a component of some imaging tools and some surgical tools. In this case, for example, if the bending portion, which is the insertion portion, of the flexible endoscope described in PTL 1 is bent at an excessively large angle, it becomes impossible for a component of some tools formed of a high-rigidity member to pass through the tool channel. In such a case, it is necessary to readjust the bending angle of the bending portion to allow the tool, which has failed to pass through the tool channel and has stuck in the tool channel, to pass, time and effort required for a manipulation increases, and, as a result, burden on a medical doctor, who performs the manipulation, and a test subject increases.

SUMMARY OF INVENTION

One or more aspects of the present disclosure have been made in consideration of the above issue, and at least one object of the present disclosure is to provide a mechanism that can reduce time and effort required for a manipulation when the manipulation is performed to insert and extract a plurality of different tools into a tool channel after a bending portion of a continuum robot has been inserted to the inside of a test body such as a test subject.

A continuum robot control system according to the present invention includes: a continuum robot including a bending portion that bends with respect to a reference axis when a linear member is driven, a driving portion that drives the linear member, and a tool channel that is a tubular path extending through an inside of the bending portion and through which a tool is to be inserted and extracted; and a control device that controls movement of the continuum robot. When a plurality of the tools that are different are inserted into and extracted from the tool channel after the bending portion has been inserted to an inside of a test body, the control device acquires, for each of the plurality of tools, a maximum value of bending angle at which the tool is capable of passing through the tool channel, sets a smallest of a plurality of the acquired maximum values of bending angle as a maximum bending angle, and controls the driving portion so that the bending portion bends within a range of the maximum bending angle.

The present invention includes a continuum robot control method using the continuum robot control system described above.

Further features of the present invention will become apparent from the following description of exemplary embodiments with reference to the attached drawings.

DESCRIPTION OF EMBODIMENTS

Hereafter, embodiments of the present invention will be described with reference to the drawings.

First Embodiment

First, a first embodiment of the present invention will be described.

In the present embodiment, an example of a continuum robot control system including a continuum robot including a bending portion that is three-dimensionally bendable and a control device that controls the continuum robot will be described. First, a configuration of the continuum robot control system according to the present embodiment will be described, and next, configurations of the continuum robot according to the present embodiment, an imaging tool, and a surgical tool will be described. Further, a method with which the control device limits the bending angle of a bending portion will be described, and lastly, an example of manipulation of sampling a specimen from a deep part of the lung of a test subject, such as a patient, will be described.

1-1. Configuration of Continuum Robot Control System

Figure 1:
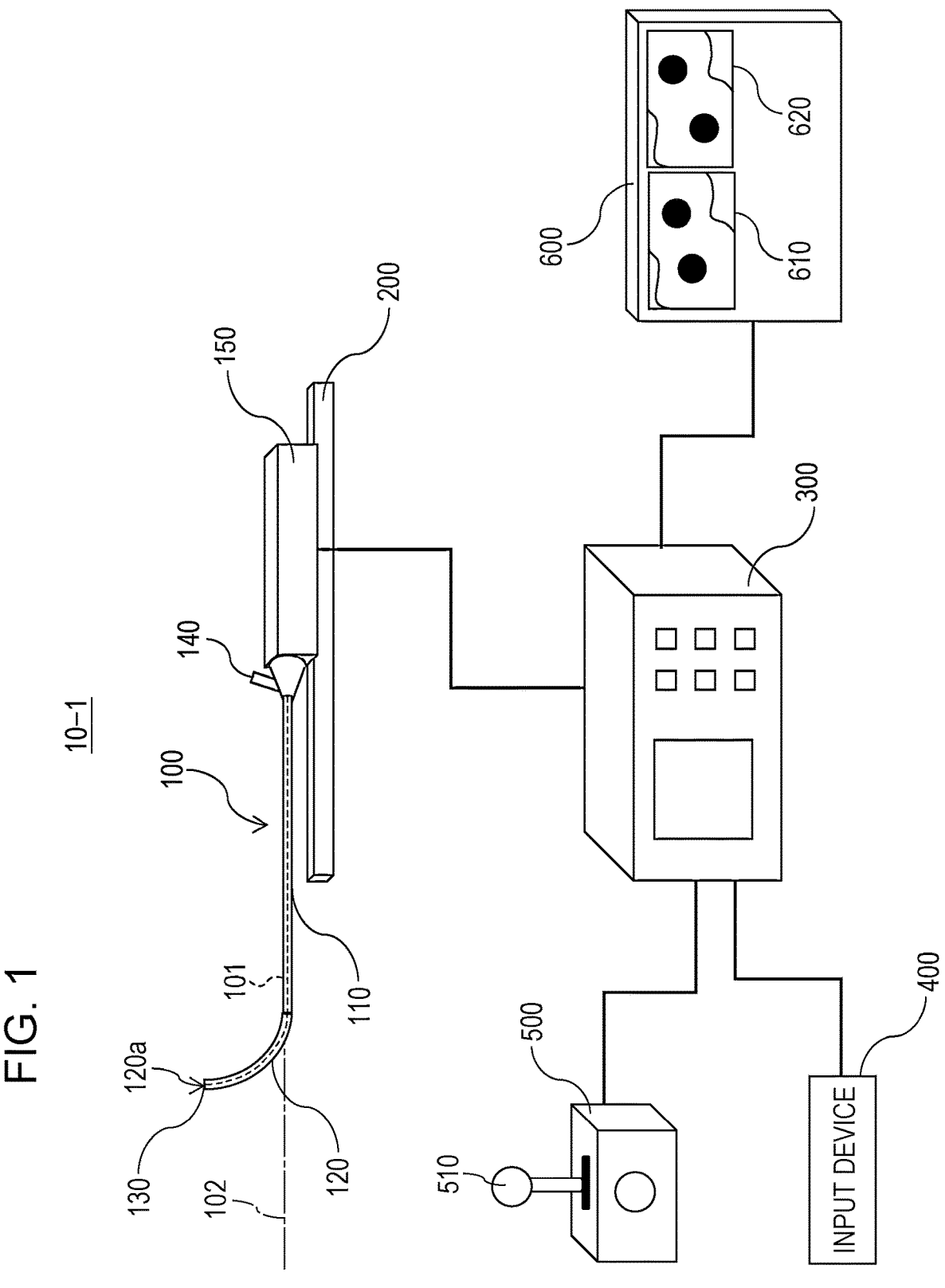
FIG. 1 is a schematic view illustrating an example of a schematic configuration of a continuum robot control system according to a first embodiment of the present invention.

FIG. 1 is a schematic view illustrating an example of a schematic configuration of a continuum robot control system 10-1 according to the first embodiment of the present invention. As illustrated in FIG. 1, the continuum robot control system 10-1 includes a continuum robot 100, a linear stage 200, a control device 300, an input device 400, an operation device 500, and an image display device 600.

As illustrated in FIG. 1, the continuum robot 100 includes an elongated portion 110, a bending portion 120, a coil 130, a tool insertion opening 140, and a driving unit 150. The continuum robot 100 further includes a tool channel 101 that is a tubular path extending through the inside of the elongated portion 110 and the bending portion 120 and through which a tool is to be inserted and extracted via the tool insertion opening 140.

The elongated portion 110 includes the tool channel 101 therein. In addition, a plurality of drive wires, corresponding to a plurality of linear members that are driven by the driving unit 150 when the bending portion 120 is to be bent with respect to a reference axis 102, are inserted through the elongated portion 110.

The bending portion 120 can actively change the posture thereof. To be specific, the bending portion 120 bends with respect to the reference axis 102 when the drive wires, which are linear members connected to the bending portion 120, are driven by an actuator (driving portion) that is set inside of the driving unit 150. Here, in the present embodiment, the reference axis 102 is an axis extending in a direction parallel to the movement direction of the continuum robot 100 on the linear stage 200.

The coil 130 is set at a distal end 120a of the bending portion 120. Although not illustrated in FIG. 1, a magnetic field generating device is set near the bending portion 120. Then, it is possible to detect the position and the direction of the distal end 120a of the bending portion 120 by reading a change in a magnetic field generated by the magnetic field generating device (not shown) via the coil 130.

The tool insertion opening 140 is provided, for example, in a joint portion (base portion) between the elongated portion 110 and the driving unit 150. The tool insertion opening 140 is an inlet through which various tools are inserted into and extracted from the tool channel 101 provided inside of the elongated portion 110 and the bending portion 120. Examples of various tools that can be inserted from the tool insertion opening 140 include an imaging tool and a surgical tool for biopsy or treatment.

The driving unit 150 includes an actuator (driving portion) that drives drive wires, which are linear members connected to the bending portion 120, when the bending portion 120 is to be bent at a desirable bending angle with respect to the reference axis 102. In the present embodiment, the driving unit 150 is fixed to the linear stage 200, and the continuum robot 100 performs a linear motion in the longitudinal direction of the linear stage 200 when a user such as a doctor pushes and pulls the driving unit 150 forward and backward.

As described above, the driving unit 150 is fixed to the linear stage 200. The linear stage 200 corresponds to a movement device that moves the continuum robot 100 forward and backward relative to a test subject (which may be a "test body" as a broader concept).

The control device 300 is a device that controls the movement of the continuum robot 100 based on, for example, an operation input from the operation device 500, an input from the input device 400, or an input from the coil 130. Moreover, the control device 300 performs various control including display control of the image display device 600 and various processing.

The input device 400 is a device that inputs various information (including various data and various images) to the control device 300.

The operation device 500 is a device that a user such as a doctor operates. The operation device 500 includes a lever 510 that a user such as a doctor operates to cause the bending portion 120 to have a desired posture. The control device 300 outputs a wire driving amount command to the actuator (driving portion) of the driving unit 150 so that the bending portion 120 has a desired posture based on the operation amount of the lever 510.

An interface for receiving an image captured by an imaging tool is provided in the control device 300, and the image that the control device 300 has received from the imaging tool is output to the image display device 600 and displayed as a camera image 610. The image display device 600 displays, in addition to the camera image 610 outputted from the imaging tool, for example, a navigation image 620 created beforehand from a 3D-model of the lung of a test subject and the like. Examples of the navigation image 620 include: a bird's eye view of a path from the distal end position of the bending portion 120 to an affected area (region of interest) of the test subject observed from the outside; and an image of the inside of the lung observed from an imaginary camera at the distal end 120a of the bending portion 120. As necessary, a user such as a doctor can switch between the camera image 610 and the navigation image 620 displayed on the image display device 600.

1-2. Configuration of Continuum Robot

Figure 2:
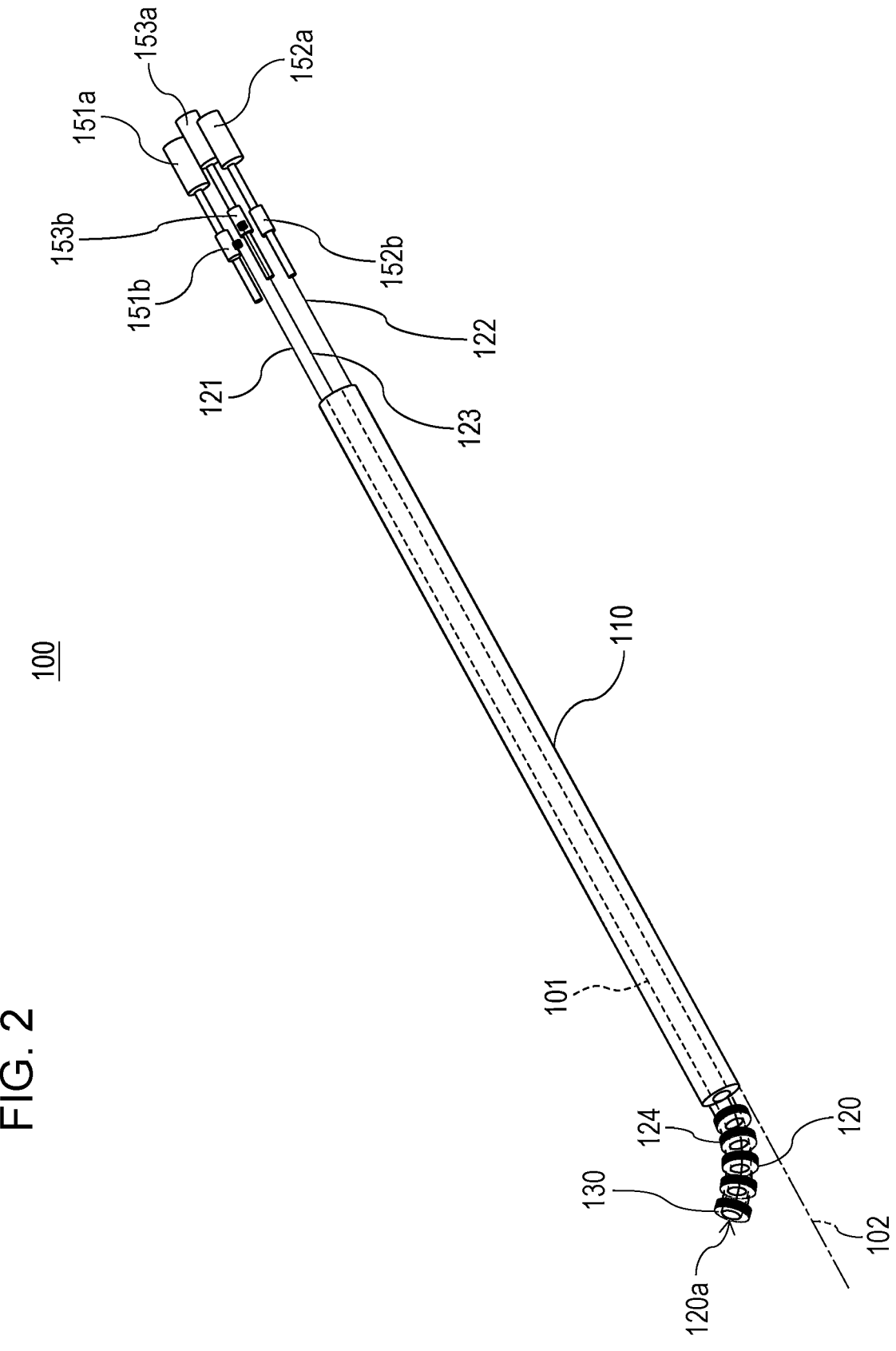
FIG. 2 is a schematic view illustrating an example of a schematic configuration of a continuum robot according to the first embodiment of the present invention.

FIG. 2 is a schematic view illustrating an example of a schematic configuration of the continuum robot 100 according to the first embodiment of the present invention. In FIG. 2, elements similar to those illustrated in FIG. 1 are denoted by the same numerals, and detailed description thereof will be omitted. FIG. 2 does not illustrate the tool insertion opening 140 illustrated in FIG. 1.

The elongated portion 110 is a member that bends passively in response to an external force.

The bending portion 120 includes a plurality of wire guides 124 that are members for guiding a plurality of drive wires 121 to 123 that are a plurality of linear members. At this time, one end of each of the three drive wires 121 to 123 is fixed and connected to a wire guide 124 disposed at the distal end 120a of the bending portion 120 and the other end of each of the three drive wires 121 to 123 is connected to a corresponding one of actuators 151a to 153a. The coil 130 described above is included, for example, in the wire guide 124 disposed at the distal end 120a of the bending portion 120.

The actuators 151a to 153a and feed screws 151b to 153b illustrated in FIG. 2 are disposed inside of the driving unit 150 illustrated in FIG. 1. To be specific, the drive wire 121 is connected to the actuator 151a via the feed screw 151b. The drive wire 122 is connected to the actuator 152a via the feed screw 152b. The drive wire 123 is connected to the actuator 153a via the feed screw 153b. It is possible to bend the bending portion 120 with respect to the reference axis 102 as each of the actuators 151a to 153a pushes and pulls a corresponding one of the drive wires 121 to 123 in the longitudinal direction of the continuum robot 100 based on control by the control device 300.

As illustrated in FIG. 2, the tool channel 101 described above is included inside of the elongated portion 110 and the bending portion 120. A user such as a doctor can insert an imaging tool or a surgical tool from the tool insertion opening 140 illustrated in FIG. 1 and cause the inserted tool to reach the distal end 120a of the bending portion 120 via the tool channel 101.

Here, behaviors of the bending portion 120 and the elongated portion 110 when the actuators 151a to 153a are driven will be described below.

Rotational movements of the actuators 151a to 153a are decelerated by the feed screws 151b to 153b connected to respective output shafts thereof and converted into translational movements. Wire grip portions for fixing the drive wires 121 to 123 are provided on the nuts of the feed screws 151b to 153b, and, when the actuators 151a to 153a are driven, the drive wires 121 to 123 are pushed and pulled in the longitudinal direction of the continuum robot 100. Since the drive wires 121 to 123 are fixed and connected to the distal end 120a of the bending portion 120 as described above, the bending portion 120 bends with respect to the reference axis 102 when the drive wires 121 to 123 are pushed and pulled. At this time, since the drive wires 121 to 123 are fixed and connected to the distal end 120a of the bending portion 120 with different phases, it is possible to bend the bending portion 120 at a desired bending angle and in a desired direction by controlling the driving amount of each of the actuators 151a to 153a. On the other hand, since the drive wires 121 to 123 are not fixed to the elongated portion 110, the posture of the elongated portion 110 does not change even when the drive wires 121 to 123 are pushed and pulled.

Next, contact between the bending portion 120 and a lumen of a test subject when the bending portion 120 is inserted to the inside of the test subject and behaviors of the bending portion 120 and the elongated portion 110 when an external force for insertion and extraction of various tools or the like is applied will be described below.

Since the elongated portion 110 is not connected to the drive wires 121 to 123, the elongated portion 110 deforms in such a way as to follow an external force when the external force acts thereon. Therefore, for example, even when the elongated portion 110 is bent, the elongated portion 110 can deform in such a way as to conform to insertion of a tool and can allow the tool to pass. On the other hand, when an external force acts on the bending portion 120, although a pushing/pulling force is generated in the drive wires 121 to 123 due to the external force, since the actuators 151a to 153a do not rotate easily due to friction of the feed screws 151*b* to 153*b* and the action of the speed reduction mechanism, the bending angle of the bending portion 120 does not change when, for example, a tool is inserted.

1-3. Configurations of Various Tools

Figure 3A:
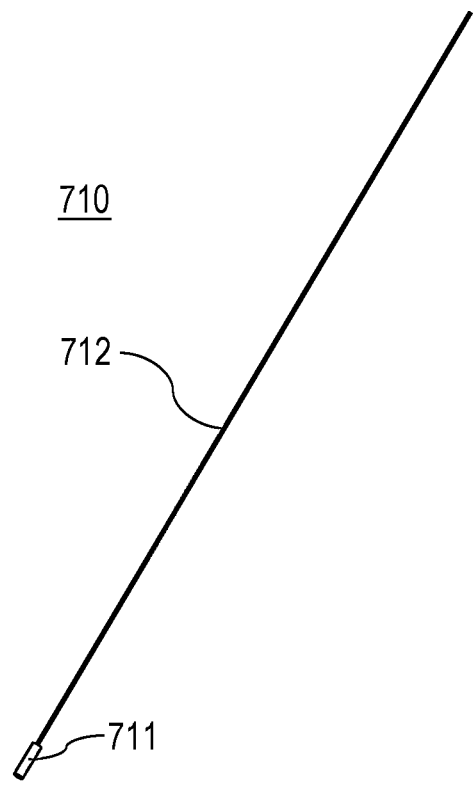
FIG. 3A illustrates the first embodiment of the present invention, and is a schematic view illustrating an example of various tools that can be inserted into and extracted from a tool channel illustrated in FIGS. 1 and 2.
Figure 3B:
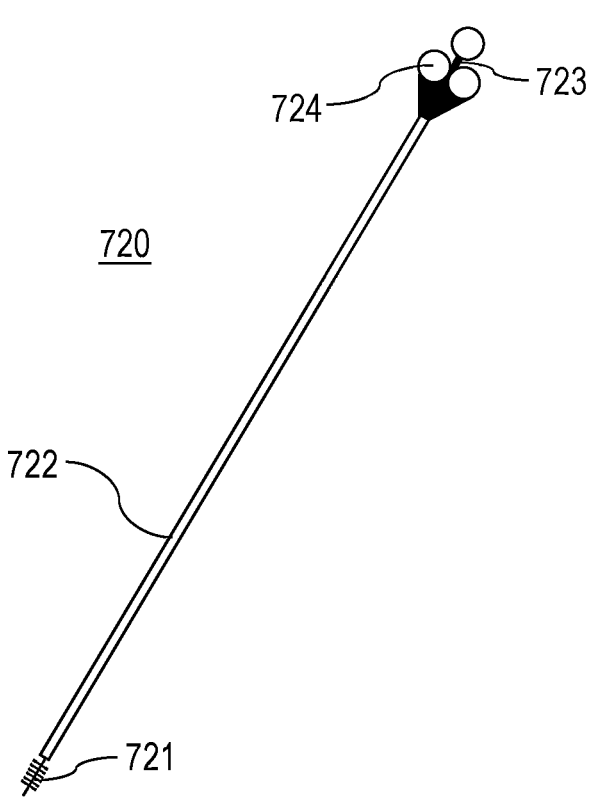
FIG. 3B illustrates the first embodiment of the present invention, and is a schematic view illustrating an example of various tools that can be inserted into and extracted from the tool channel illustrated in FIGS. 1 and 2.
Figure 3C:
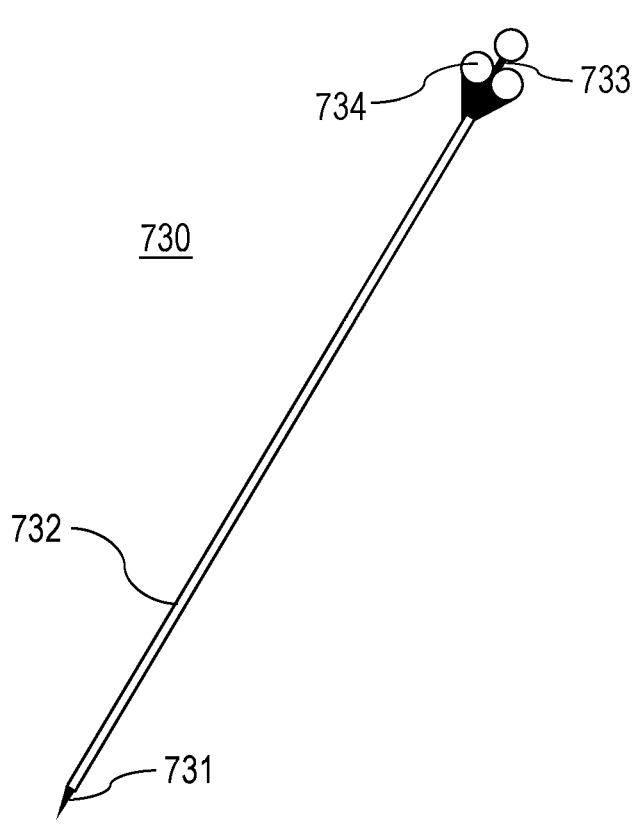
FIG. 3C illustrates the first embodiment of the present invention, and is a schematic view illustrating an example of various tools that can be inserted into and extracted from the tool channel illustrated in FIGS. 1 and 2.

FIGS. 3A to 3C illustrate the first embodiment of the present invention, and are schematic views each illustrating an example of various tools that can be inserted into and extracted from the tool channel 101 illustrated in FIGS. 1 and 2.

FIG. 3A is a schematic view of an imaging tool 710. As illustrated in FIG. 3A, the imaging tool 710 includes an imaging unit 711 and a camera cable 712. The imaging unit 711 includes an objective optical system and an illumination optical system (not shown) and can capture an image of the inside of the body of a test subject. Inside of the camera cable 712, a signal cable for transmitting image information obtained by the objective optical system described above and a power cable for supplying electric power to the illumination optical system described above are disposed. Being constituted by a low-rigidity member, the camera cable 712 can be inserted through the tool channel 101 even when the continuum robot 100 is bent. On the other hand, the imaging unit 711 is constituted by a high-rigidity member in order to protect the optical systems. As described above, since the bending angle of the bending portion 120 does not change due to insertion of a tool, when the imaging tool 710 is inserted into the tool channel 101 in a state in which the bending portion 120 is bent at a large angle, the imaging unit 711 sticks in a middle part of the tool channel 101 and cannot proceed to the distal end 120*a* of the bending portion 120.

FIG. 3B is a schematic view of a biopsy brush tool 720, which is one of surgical tools. As illustrated in FIG. 3B, the biopsy brush tool 720 includes a brush 721, a sheath 722, a cable 723, and an operation portion 724. The brush 721 is connected to the operation portion 724 via the cable 723, and it is possible to store the brush 721 in the sheath 722 and to expose the brush 721 from the sheath 722 by pulling and pushing the operation portion 724. When the biopsy brush tool 720 is to be inserted into the tool channel 101 of the continuum robot 100, the brush 721 is stored in the sheath 722 so as not to damage the continuum robot 100. On the other hand, when a tissue of an affected area (region of interest) of a test subject is to be sampled by using the biopsy brush tool 720, the brush 721 is exposed from the sheath 722. Since the sheath 722 and the cable 723 of the biopsy brush tool 720 are constituted by low-rigidity members, it is possible to insert/extract the biopsy brush tool 720 into/from the tool channel 101 even when the continuum robot 100 is bent. However, since the joint portion between the brush 721 and the cable 723 is constituted by a high-rigidity member as with the imaging unit 711 described above, when the biopsy brush tool 720 is inserted into the tool channel 101 in a state in which the bending portion 120 is bent at a large angle, the joint portion sticks in a middle part of the tool channel 101 and cannot proceed to the distal end 120*a* of the bending portion 120.

FIG. 3C is a schematic view of a biopsy needle tool 730, which is one of surgical tools. As illustrated in FIG. 3C, the biopsy needle tool 730 includes a hollow needle 731, a sheath 732, a cable 733, and an operation portion 734. The hollow needle 731 is connected to the operation portion 734 via the cable 733, and it is possible to expose the hollow needle 731 from the sheath 732 by pushing the operation portion 734. Since the sheath 732 and the cable 733 of the biopsy needle tool 730 are constituted by low-rigidity members, it is possible to insert/extract the biopsy needle tool 730 into/from the tool channel 101 even when the continuum robot 100 is bent. However, since the hollow needle 731 is constituted by a high-rigidity member as with the imaging unit 711 described above, when the biopsy needle tool 730 is inserted into the tool channel 101 in a state in which the bending portion 120 is bent at a large angle, the hollow needle 731 sticks in a middle part of the tool channel 101 and cannot proceed to the distal end 120*a* of the bending portion 120.

1-4. Configuration of Control Device

Figure 4:
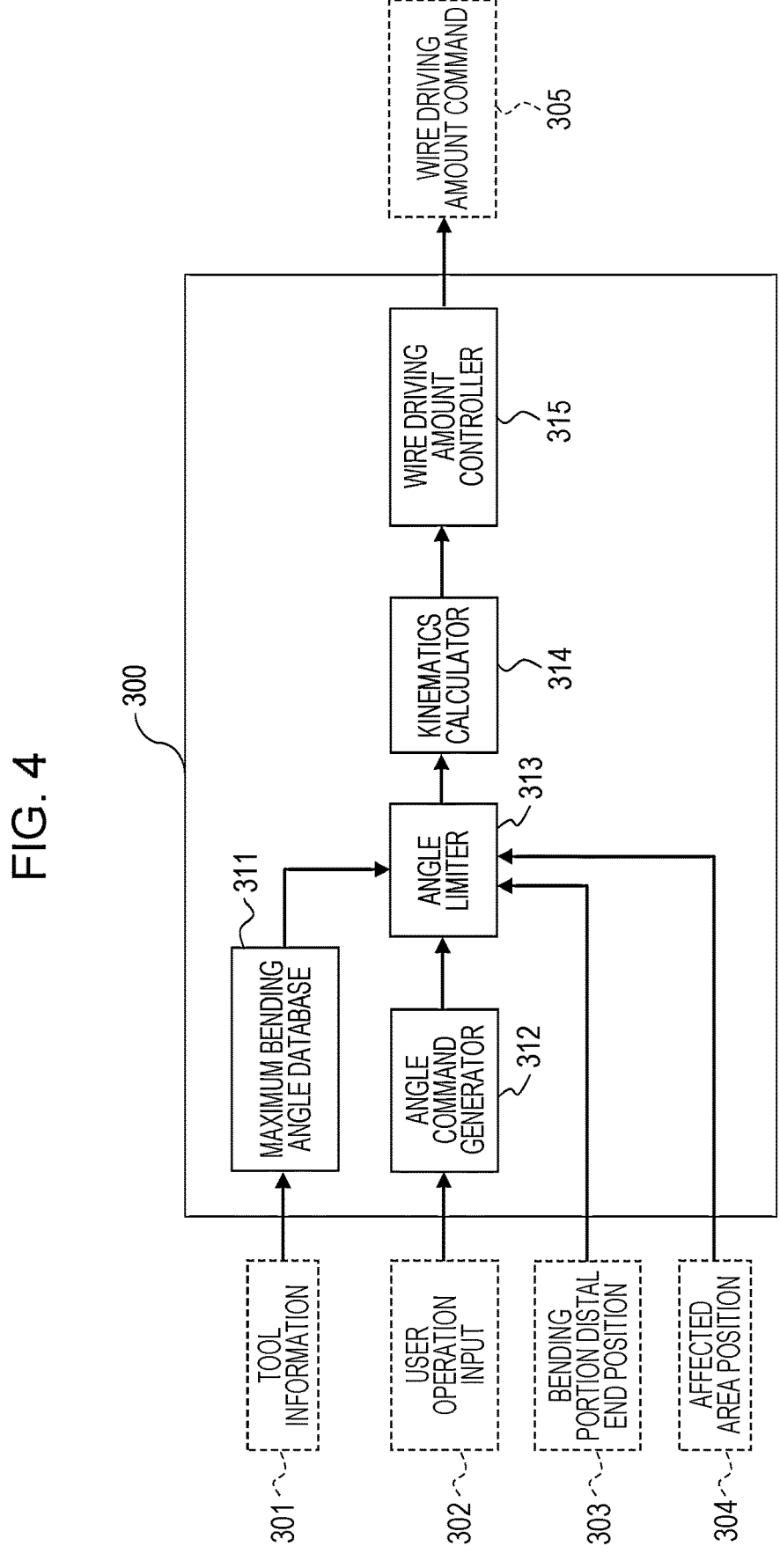
FIG. 4 is a schematic view illustrating an example of a schematic configuration of a control device according to the first embodiment of the present invention.

FIG. 4 is a schematic view illustrating an example of a schematic configuration of the control device 300 according to the first embodiment of the present invention.

The control device 300 illustrated in FIG. 4 includes a maximum bending angle database 311, an angle command generator 312, an angle limiter 313, a kinematics calculator 314, and a wire driving amount controller 315.

In FIG. 4, tool information 301 is information about the types of tools to be used in surgery or the like that a user such as a doctor has input beforehand from the input device 400. A user operation input 302 is input information about an operation amount when a user such as a doctor operates the lever 510 of the operation device 500. A bending portion distal end position 303 is position information about the distal end 120*a* of the bending portion 120 measured by the coil 130. An affected area position 304 is position information about an affected area that is a region of interest of a test subject that a user such as a doctor has determined beforehand and inputted from the input device 400.

In the maximum bending angle database 311, for each of a plurality of tools that are different and that can be used by a user (such as the imaging tool 710, the biopsy brush tool 720, and the biopsy needle tool 730 illustrated in FIGS. 3A to 3C), the maximum value of bending angle at which the tool is capable of passing through the tool channel 101 is recorded. The maximum bending angle database 311 acquires, for each of the plurality of tools according to the inputted tool information 301, the maximum value of bending angle at which the tool is capable of passing through the tool channel 101, and sets the smallest of a plurality of the acquired maximum values of bending angle as a maximum bending angle $\theta_{lim}$, and outputs the maximum bending angle $\theta_{lim}$.

The angle command generator 312 calculates a bending angle command value $\theta_{cmd}$ of the bending portion 120 based on the inputted user operation input 302.

The angle limiter 313 sets and outputs a target bending angle $\theta_{ref}$ in consideration of limitation on the bending angle of the bending portion 120, based on the bending portion distal end position 303 and the affected area position 304 that have been inputted, the maximum bending angle $\theta_{lim}$ outputted from the maximum bending angle database 311, and the bending angle command value $\theta_{cmd}$ generated by the angle command generator 312.

The kinematics calculator 314 calculates, by using the kinematics of the continuum robot 100, target wire driving amounts of the drive wires 121 to 123 for causing the bending angle of the bending portion 120 to be the target bending angle $\theta_{ref}$.

The wire driving amount controller 315 outputs a wire driving amount command 305 to the actuators 151*a* to 153*a* so that the driving amounts of the drive wires 121 to 123 coincide with the target wire driving amounts calculated by the kinematics calculator 314.

Figure 5:
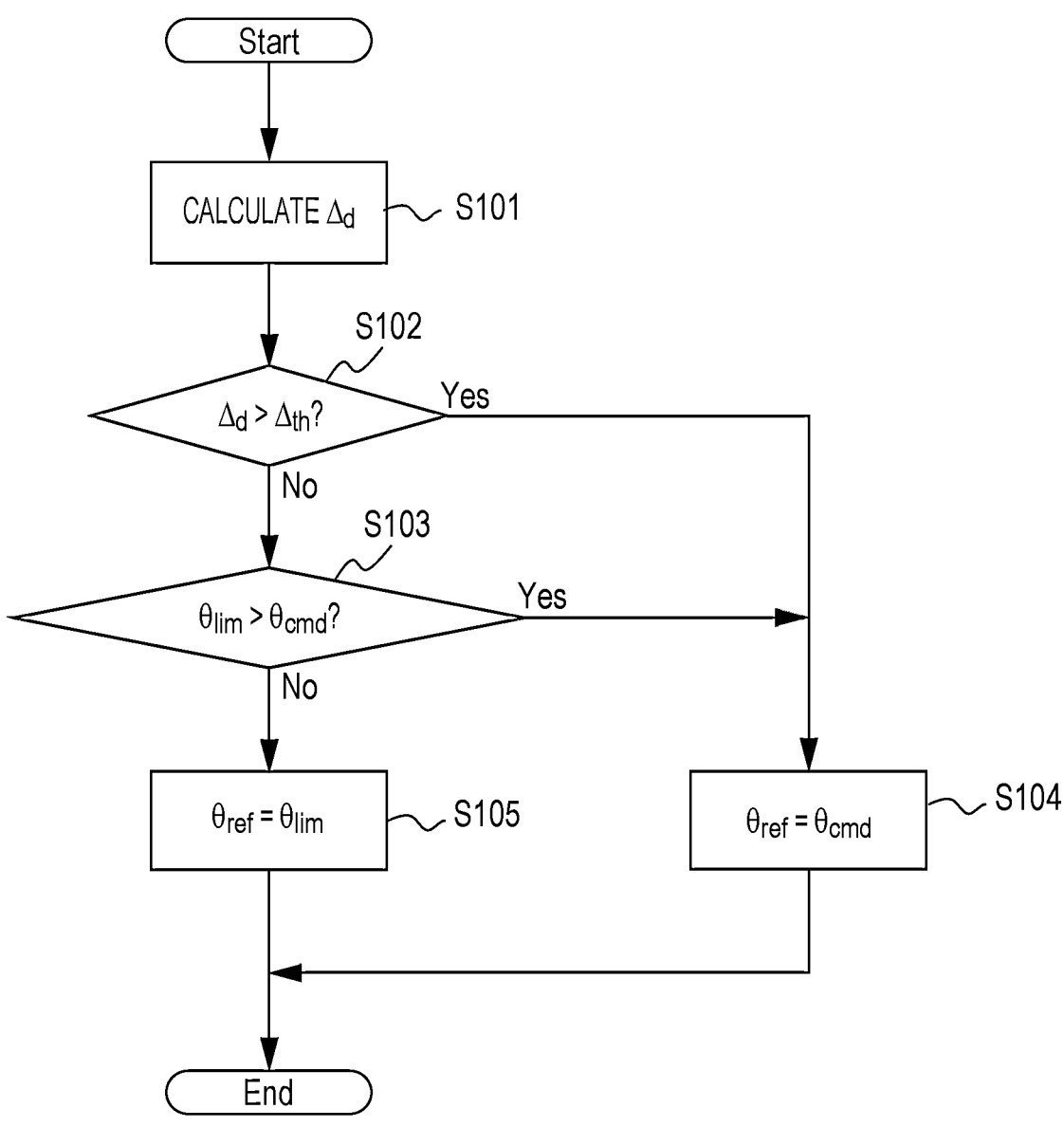
FIG. 5 is a flowchart illustrating an example of a process performed by an angle limiter of the control device illustrated in FIG. 4.

FIG. 5 is a flowchart illustrating an example of a process performed by the angle limiter 313 of the control device 300 illustrated in FIG. 4.

In the present embodiment, the angle limiter 313 sets the target bending angle $\theta_{ref}$ of the bending portion 120 to be a bending angle less than or equal to the maximum bending angle $\theta_{lim}$ only when the distal end 120a of the bending portion 120 reaches the vicinity of an affected area (region of interest) of a test subject. Therefore, the angle limiter 313 sets the bending angle command value $\theta_{cmd}$ itself as the target bending angle $\theta_{ref}$ of the bending portion 120 when the distal end 120a of the bending portion 120 is apart from the affected area (region of interest) of the test subject.

To be specific, first, in step S101 of FIG. 5, the angle limiter 313 calculates the distance $\Delta_d$ between the bending portion distal end position 303 measured by the coil 130 and the affected area position 304.

Next, in step S102, the angle limiter 313 determines whether or not the distance $\Delta_d$ calculated in step S101 is greater than a threshold $\Delta_{th}$.

If it is determined in step S102 that the distance $\Delta_d$ calculated in step S101 is not greater than the threshold $\Delta_{th}$ (the distance $\Delta_d$ is less than or equal to the threshold $\Delta_{th}$) (S102/No), the process proceeds to step S103.

In step S103, the angle limiter 313 determines whether or not the maximum bending angle $\theta_{lim}$ outputted from the maximum bending angle database 311 is greater than the bending angle command value $\theta_{cmd}$ generated by the angle command generator 312.

If it is determined in step S103 that the maximum bending angle $\theta_{lim}$ is greater than the bending angle command value $\theta_{cmd}$ (S103/Yes) or if it is determined in step S102 that the distance $\Delta_d$ is greater than the threshold $\Delta_{th}$ (S102/Yes), the process proceeds to step S104.

In step S104, the angle limiter 313 sets the bending angle command value $\theta_{cmd}$ generated by the angle command generator 312 as the target bending angle $\theta_{ref}$ of the bending portion 120, and outputs the target bending angle $\theta_{ref}$.

On the other hand, if it is determined in step S103 that the maximum bending angle $\theta_{lim}$ is not greater than the bending angle command value $\theta_{cmd}$ ((the maximum bending angle $\theta_{lim}$ is less than or equal to the bending angle command value $\theta_{cmd}$) (S103/No), the process proceeds to step S105.

In step S105, the angle limiter 313 sets the maximum bending angle $\theta_{lim}$ outputted from the maximum bending angle database 311 as the target bending angle $\theta_{ref}$ of the bending portion 120, and outputs the target bending angle $\theta_{ref}$.

If processing in step S104 has finished or processing in step S105 has finished, the process of the flowchart of FIG. 5 finishes.

With the process of the flowchart of FIG. 5 described above, the control device 300 performs control as follows.

If the bending angle command value $\theta_{cmd}$ of the bending portion 120 based on an operation input of a user is less than the maximum bending angle $\theta_{lim}$ (S103/Yes), the control device 300 controls the actuators 151a to 153a, which are driving portions, by using the bending angle command value $\theta_{cmd}$ as the target bending angle $\theta_{ref}$ of the bending portion 120.

If the bending angle command value $\theta_{cmd}$ of the bending portion 120 is greater than or equal to the maximum bending angle described above (S103/No), the control device 300 controls the actuators 151a to 153a, which are driving portions, by using the maximum bending angle $\theta_{lim}$ as the target bending angle $\theta_{ref}$ of the bending portion 120.

1-5. Process of Lung Biopsy

A process of performing lung biopsy of a test subject by using the continuum robot 100 described above, the various tools 710 to 730 illustrated in FIGS. 3A to 3C, and the control device 300 will be described. A user creates beforehand a 3D-model of the lung of the test subject from medical images such as an MRI image and a CT image of the lung. Subsequently, with reference to the created 3D-model, the user determines a target position (the position of a region of interest) from which a tissue is to be sampled and a target path along which the distal end 120a of the bending portion 120 of the continuum robot 100 passes to reach the target position. Then, the user stores, together with the created 3D-model, information about the determined target position and target path in a storage (not shown) of the control device 300. Moreover, the user inputs beforehand information about the types and the like of tools to be actually used in the surgery (manipulation) from the input device 400 to the control device 300 as the tool information 301. In this case, the maximum bending angle database 311 acquires, for each of the plurality of tools according to inputted tool information 301, the maximum value of bending angle at which the tool is capable of passing through the tool channel 101, and sets the smallest of a plurality of the acquired maximum values of bending angle as a maximum bending angle $\theta_{lim}$.

FIGS. 6A to 6D illustrate the first embodiment of the present invention, and are schematic views illustrating behaviors of the continuum robot 100 and various tools inside the lung of a test subject. In FIGS. 6A to 6D, elements similar to those illustrated in FIGS. 1 to 3C are denoted by the same numerals, and detailed description thereof will be omitted.

When surgery is started, a user such as a doctor first inserts the imaging tool 710 into the tool channel 101 of the continuum robot 100 to insert the imaging unit 711, which is located at the distal end of the imaging tool 710, to the distal end of the bending portion 120. Next, the user inserts the continuum robot 100, into which the imaging tool 710 has been inserted, from the mouth or nose of the test subject. Then, the user operates the operation device 500 (the lever 510 and the like) while referring to the camera image 610 and the navigation image 620 displayed on the image display device 600, and moves the linear stage 200, on which the driving unit 150 of the continuum robot 100 is placed, forward while controlling the posture of the distal end 120a of the bending portion 120 so that the distal end 120a of the bending portion 120 may not press a lumen of the test subject.

Figure 6A:
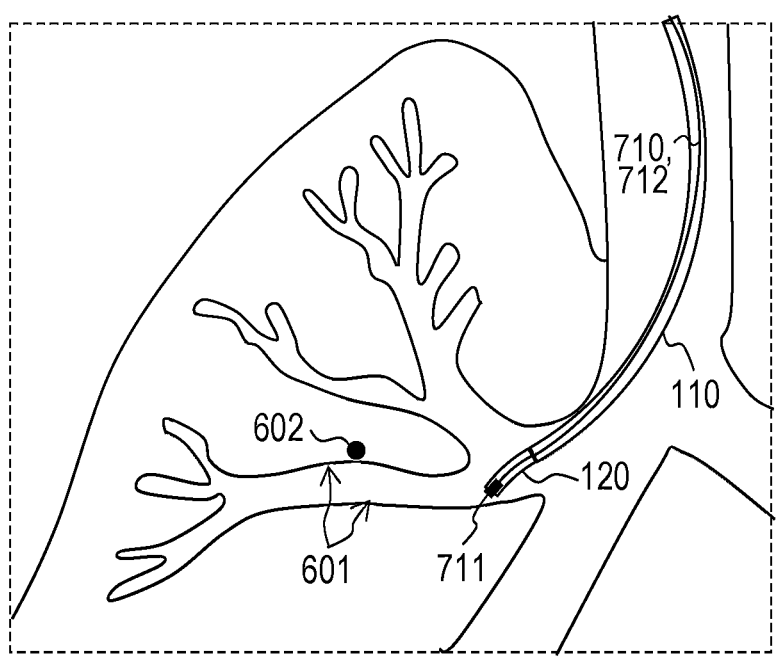
FIG. 6A illustrates the first embodiment of the present invention, and is a schematic view illustrating behaviors of the continuum robot and various tools inside of the lung of a test subject.

As illustrated in FIG. 6A, when the distal end of the bending portion 120 of the continuum robot 100 reaches a branching portion of a lumen 601 of the lung of the test subject, the user checks the position of an affected area 602, which is the region of interest of the test subject, by referring to the navigation image 620. Then, the user moves the linear stage 200, on which the driving unit 150 of the continuum robot 100 is placed, forward while orienting the distal end of the bending portion 120 toward the target path in the lumen 601 of the lung of the test subject.

Before the distal end of the bending portion 120 reaches the vicinity of the affected area 602 from the inlet of the bronchus of the test subject, the control device 300 does not limit the bending angle of the bending portion 120, because the distance $\Delta_d$ between the distal end position of the bending portion 120 of the continuum robot 100 and the position of the affected area 602 is greater than the threshold $\Delta_{th}$. Therefore, the user can operate the posture of the bending portion 120 to be at a desired bending angle.

Figure 6B:
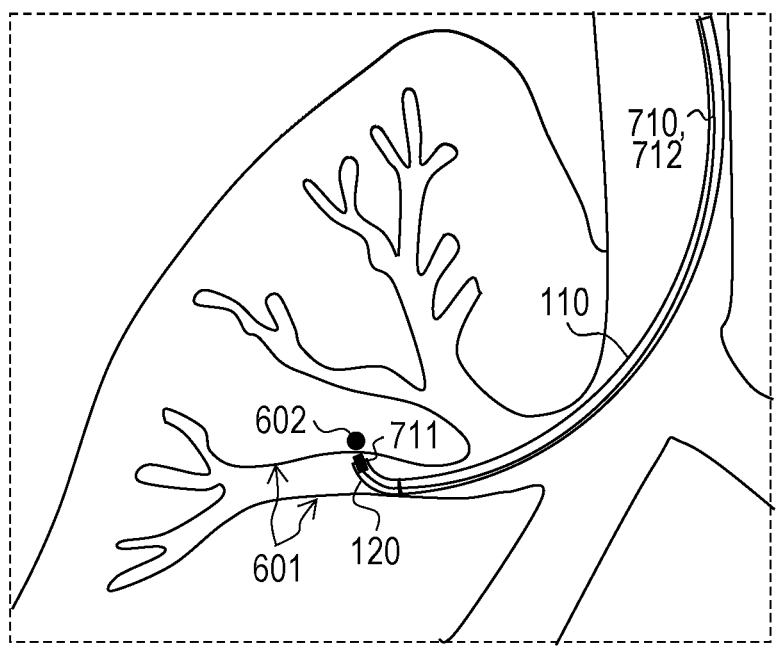
FIG. 6B illustrates the first embodiment of the present invention, and is a schematic view illustrating behaviors of the continuum robot and various tools inside the lung of a test subject.

When the distal end of the bending portion 120 reaches the vicinity of the affected area 602 along the lumen 601 of the lung of the test subject, the user operates the operation device 500 (the lever 510 and the like) to adjust the bending angle of the bending portion 120 so that the distal end of the bending portion 120 orients toward the affected area 602 as illustrated in FIG. 6B. At this time, since the distance $\Delta_d$ is less than or equal to the threshold $\Delta_{th}$, the angle limiter 313 sets the target bending angle $\theta_{ref}$ of the bending portion 120 to be within the range of the maximum bending angle $\theta_{lim}$ (less than or equal to the maximum bending angle $\theta_{lim}$) such that all of the tools to be used can pass through the tool channel 101.

Figure 6C:
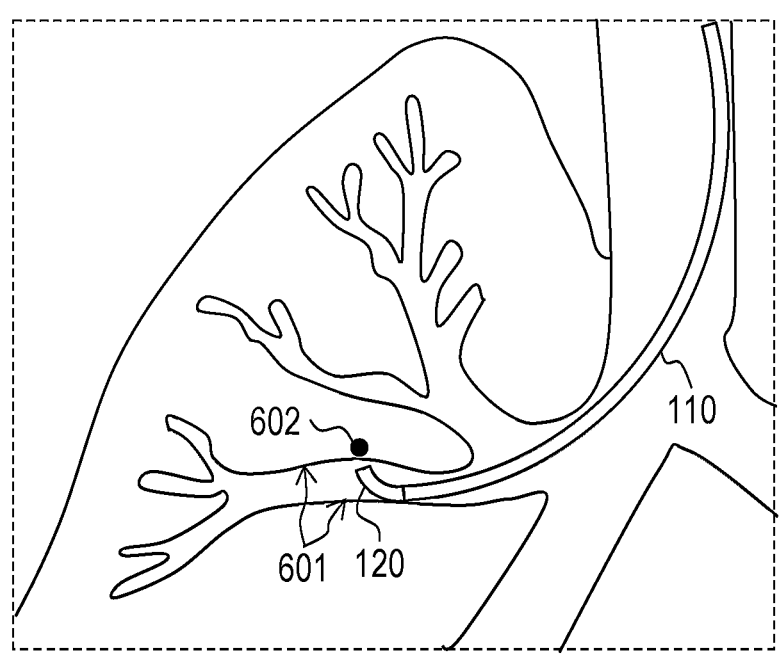
FIG. 6C illustrates the first embodiment of the present invention, and is a schematic view illustrating behaviors of the continuum robot and various tools inside the lung of a test subject.

Then, after the adjustment has finished, as illustrated in FIG. 6C, the user extracts the imaging tool 710 from the tool channel 101 of the continuum robot 100.

Figure 6D:
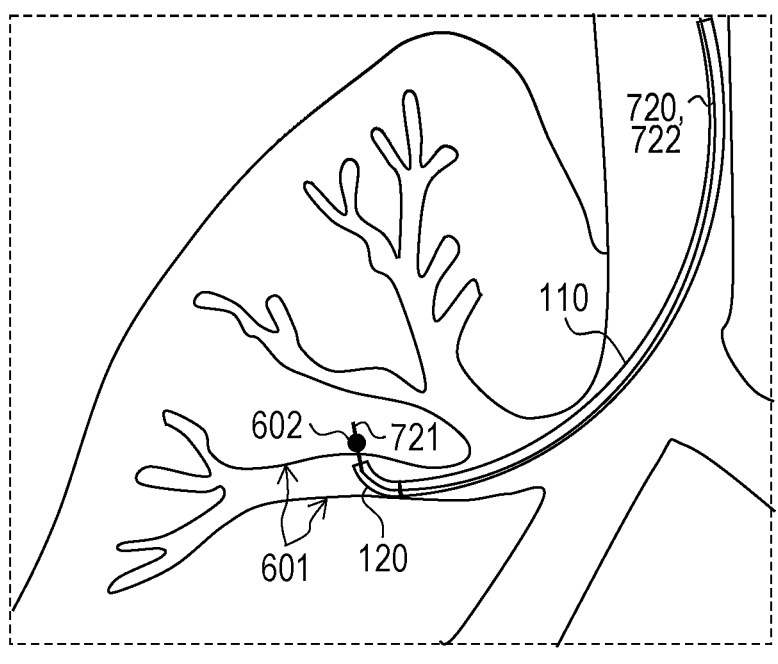
FIG. 6D illustrates the first embodiment of the present invention, and is a schematic view illustrating behaviors of the continuum robot and various tools inside the lung of a test subject.

Next, as illustrated in FIG. 6D, the user inserts the biopsy brush tool 720 into the tool channel 101 of the continuum robot 100, and samples a tissue from the affected area 602, which is the region of interest of the test subject, by using the brush 721 at the distal end thereof.

Next, when sampling of the tissue from the affected area 602 using the biopsy brush tool 720 has finished, the user extracts the biopsy brush tool 720 from the tool channel 101 of the continuum robot 100. Subsequently, the user inserts the biopsy needle tool 730 into the tool channel 101 of the continuum robot 100, and samples a tissue from the affected area 602 by using a method similar to that of the biopsy brush tool 720. At this time, the biopsy needle tool 730 can also pass through the tool channel 101 to reach the affected area 602, because the angle limiter 313 has set the maximum bending angle $\theta_{lim}$ so that all of the tools 710 to 730 to be used can pass through the tool channel 101.

Subsequently, when sampling of the tissue from the affected area 602 using the biopsy needle tool 730 has finished, the user extracts the biopsy needle tool 730 from the tool channel 101 of the continuum robot 100. Next, the user inserts the imaging tool 710 into the tool channel 101 of the continuum robot 100 again, and checks that the vicinity of the affected area 602 does not have severe bleeding. Lastly, the user moves the linear stage 200, on which the driving unit 150 of the continuum robot 100 is placed, backward to extract the continuum robot 100 from the lung of the test subject.

The control device 300 of the continuum robot control system 10-1 according to the first embodiment performs the following process.

To be specific, when the plurality of tools 710 to 730 that are different are inserted into and extracted from the tool channel 101 after the bending portion 120 of the continuum robot 100 has been inserted to the inside of a test subject (which may be a "test body" as a broader concept), the control device 300 acquires, for each of the plurality of tools 710 to 730, the maximum value of bending angle at which the tool is capable of passing through the tool channel 101. Then, the control device 300 sets the smallest of a plurality of the acquired maximum values of bending angle as a maximum bending angle $\theta_{lim}$, and controls the actuators 151a to 153a in the driving unit 150, which are a driving portion, so that the bending portion 120 bends within the range of the maximum bending angle $\theta_{lim}$.

With such a configuration, when a manipulation such that a plurality of different tools are inserted and extracted is performed, it is possible to orient the distal end 120a of the bending portion 120 toward the affected area 602, which is the region of interest of a test subject (test body), while limiting the bending angle of the bending portion 120 so that all of the plurality of tools are capable of being inserted through the tool channel 101. That is, with such a configuration, when a manipulation such that a plurality of different tools are inserted into and extracted from the tool channel 101 after the bending portion 120 of the continuum robot 100 has been inserted to the inside of the test body is performed, it is possible to reduce time and effort required for the manipulation.

Moreover, the control device 300 of the continuum robot control system 10-1 according to the first embodiment performs the following process.

To be specific, if the distance $\Delta_d$ between the distal end position of the bending portion 120 and the position of the affected area 602, which is the region of interest of a test subject (test body), is less than or equal to a threshold (less than or equal to the threshold $\Delta_{th}$), the control device 300 controls the actuators 151a to 153a, which are driving portions, so that the bending portion 120 bends within the range of the maximum bending angle $\theta_{lim}$ described above.

With such a configuration, since the bending angle of the bending portion 120 is limited only when the distal end 120a of the bending portion 120 reaches the vicinity of the affected area 602, an operation by a user is not obstructed when the bending portion 120 proceeds inside of the lumen 601 of the test subject (test body).

The first embodiment also includes a method (continuum robot control method) of a process performed by the continuum robot control system 10-1.

Second Embodiment

Next, a second embodiment of the present invention will be described. In the following description of the second embodiment, description of matters common to those of the first embodiment described above will be omitted, and matters different from those of the first embodiment described above will be described.

In the second embodiment, a configuration of limiting the movement amount of a linear stage that moves the continuum robot 100 forward and backward, in addition to limiting the bending angle of the bending portion 120 described above in the first embodiment, will be described.

In order to increase the success rate of sampling of a tissue from the affected area 602 described with reference to FIGS. 6A to 6D in the first embodiment, it is desirable to control the linear stage to be at an appropriate position relative to the affected area 602. This is because, if the movement amount of the linear stage is small and a tissue is attempted to be sampled in a state in which the distal end of the bending portion 120 is apart from the affected area 602, a tool may deflect after protruding from the distal end of the bending portion 120, and a tissue might not be sampled from a desired portion. If the movement amount of the linear stage is too large and the bending portion 120 enters a part deeper than the affected area 602, it is necessary to bend the bending portion 120 at an acute angle to orient the distal end of the bending portion 120 toward the affected area 602, and a tool cannot be inserted.

Therefore, the second embodiment has a configuration such that the maximum value of movement amount of the stage is limited so that the bending portion 120 can be oriented toward the affected area 602 even when the bending angle of the bending portion 120 reaches the maximum bending angle $\theta_{lim}$.

2-1. Configuration of Continuum Robot Control System

Figure 7:
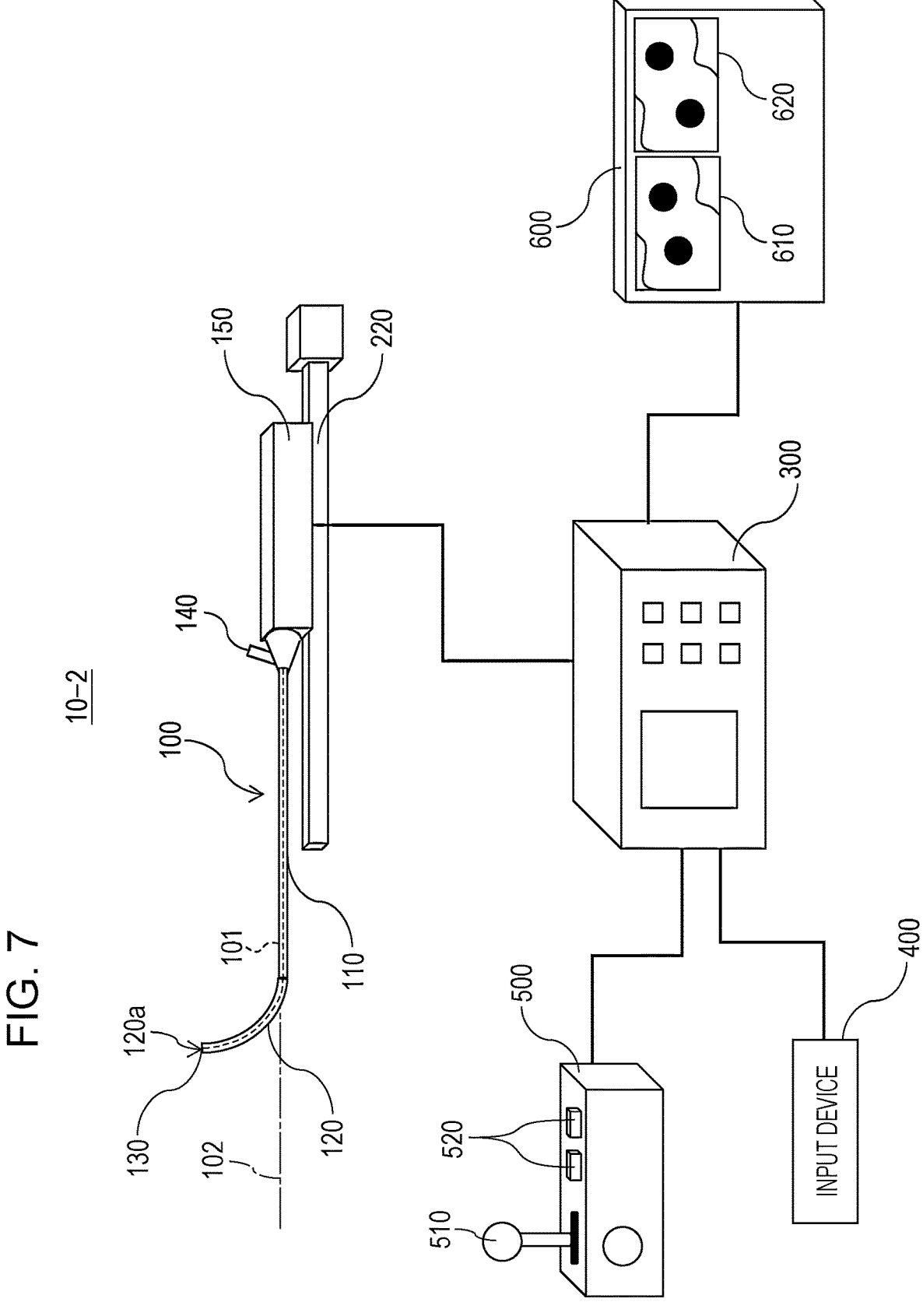
FIG. 7 is a schematic view illustrating an example of a schematic configuration of a continuum robot control system according to a second embodiment of the present invention.

FIG. 7 is a schematic view illustrating an example of a schematic configuration of a continuum robot control system 10-2 according to the second embodiment of the present invention. As illustrated in FIG. 7, the continuum robot control system 10-2 includes the continuum robot 100, an electric stage 220, the control device 300, the input device 400, the operation device 500, and the image display device 600. Here, in FIG. 7, elements similar to those illustrated in FIG. 1 are denoted by the same numerals, and detailed description thereof will be omitted.

In the second embodiment, instead of the linear stage 200 illustrated in FIG. 1, the electric stage 220, in which a stage (table) is driven by an actuator (not shown), is used. The electric stage 220 corresponds to a movement device that moves the continuum robot 100 forward and backward relative to a test subject (which may be a "test body" as a broader concept). The operation device 500 includes, in addition to the lever 510 illustrated in FIG. 1, forward/backward movement buttons 520 (a forward button and a backward button) for outputting a forward/backward movement command of the electric stage 220. In the present embodiment, when a user presses one of the forward/backward movement buttons 520, the control device 300 outputs a drive command to the actuator of the electric stage 220 in accordance with the type of the pressed button. Then, when the actuator of the electric stage 220 is driven, the table of the electric stage 220 moves, and the driving unit 150 placed on the table performs forward/backward movement. An encoder (not shown) is connected to the actuator of the electric stage 220, and the control device 300 calculates the movement amount of the table based on an input/output of the encoder.

2-2. Configuration of Control Device

Figure 8:
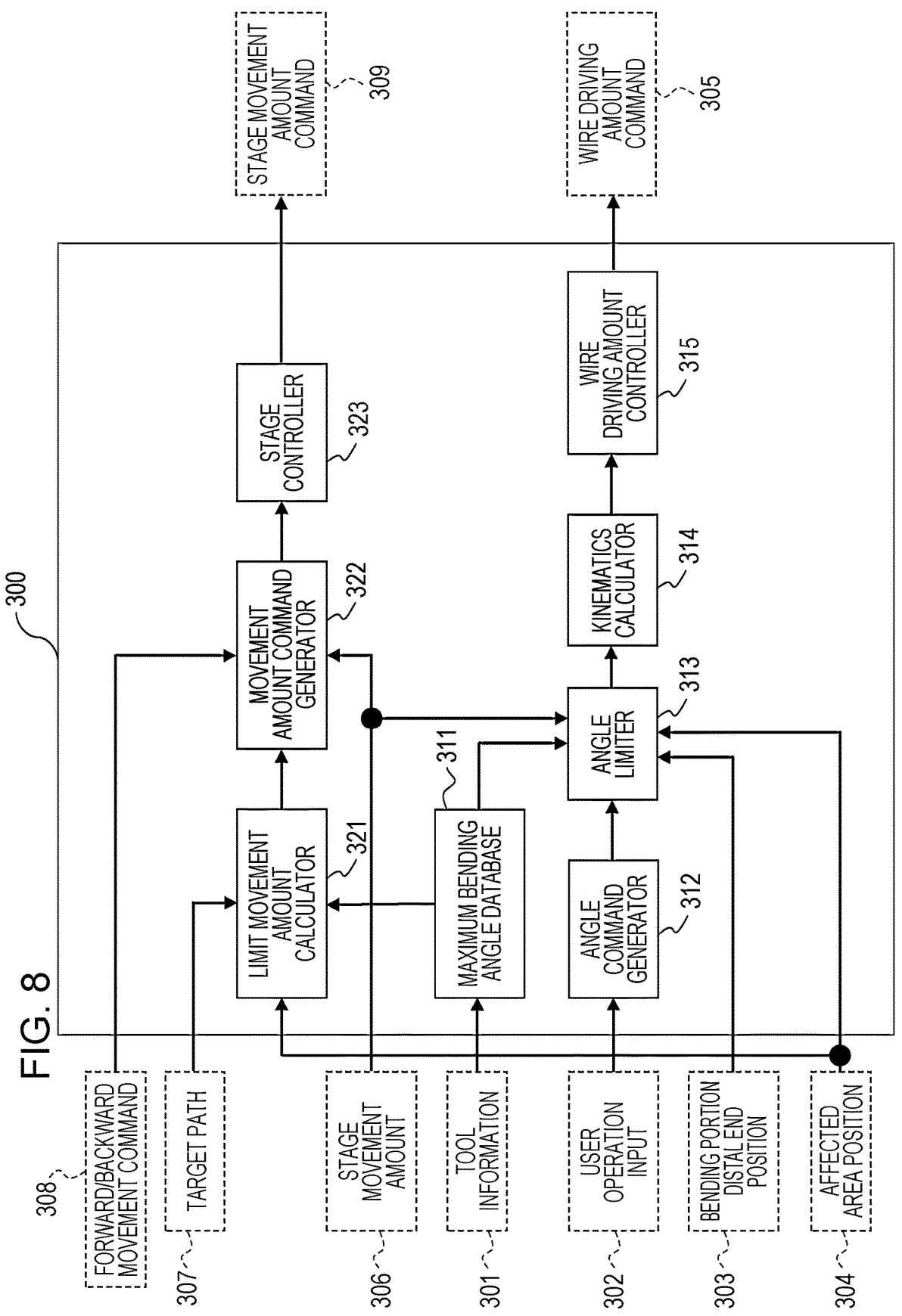
FIG. 8 is a schematic view illustrating an example of a schematic configuration of a control device according to the second embodiment of the present invention.

FIG. 8 is a schematic view illustrating an example of a schematic configuration of the control device 300 according to the second embodiment of the present invention. In FIG. 8, elements similar to those illustrated in FIG. 4 are denoted by the same numerals, and detailed description thereof will be omitted.

The control device 300 illustrated in FIG. 8 includes the maximum bending angle database 311, the angle command generator 312, the angle limiter 313, the kinematics calculator 314, the wire driving amount controller 315, a limit movement amount calculator 321, a movement amount command generator 322, and a stage controller 323. That is, in the control device 300 illustrated in FIG. 8, the limit movement amount calculator 321, the movement amount command generator 322, and the stage controller 323, which correspond to the control system of the electric stage 220, are added to the control device 300 according to the first embodiment illustrated in FIG. 4.

In FIG. 8, the tool information 301, the user operation input 302, the bending portion distal end position 303, the affected area position 304, and the wire driving amount command 305 are similar to those in FIG. 4. In FIG. 8, a stage movement amount 306 is, for example, information about a stage movement amount obtained from an encoder connected to the actuator of the electric stage 220 described above. A target path 307 is information about a target path to the affected area 602 (the region of interest of a test subject) that a user such as a doctor has determined beforehand and inputted from the input device 400. A forward/backward movement command 308 is information about a forward/backward movement command of the electric stage 220 that is outputted from the operation device 500 when a user such as a doctor operates the forward/backward movement buttons 520 of the operation device 500.

The limit movement amount calculator 321 performs repeated calculations described below to calculate the maximum movement amount $zb_{lim}$ of the electric stage 220 when orienting the distal end of the bending portion 120 toward the affected area 602 in a state in which the bending portion 120 is bent at the maximum bending angle $\theta_{lim}$, based on the affected area position 304 and the target path 307 that have been inputted and the maximum bending angle $\theta_{lim}$ outputted from the maximum bending angle database 311.

When the forward/backward movement command 308 is inputted during surgery, the movement amount command generator 322 calculates $z_b'$ by adding a very small amount to a present stage movement amount $z_b$ based on the stage movement amount 306, and outputs $z_b'$ as a target movement amount $zb_{ref}$ if the calculated $z_b'$ is less than or equal to the maximum movement amount $zb_{lim}$. The movement amount command generator 322 outputs the maximum movement amount $zb_{lim}$ as the target movement amount $zb_{ref}$ if the calculated $z_b'$ is greater than the maximum movement amount $zb_{lim}$.

The stage controller 323 outputs a stage movement amount command 309 to the electric stage 220 so that the movement amount of the electric stage 220 coincides with the target movement amount $zb_{ref}$.

Figure 9:
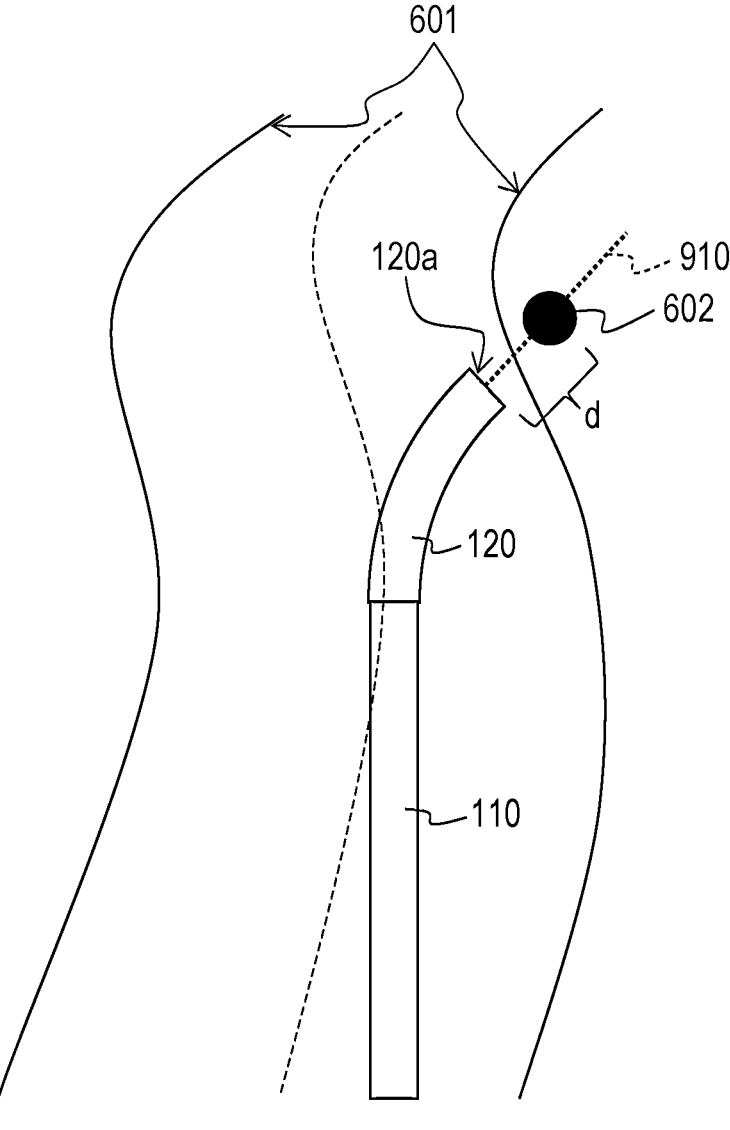
FIG. 9 is a view for describing a method of calculating a maximum movement amount by using a limit movement amount calculator of the control device illustrated in FIG. 8.

FIG. 9 is a view for describing a method of calculating the maximum movement amount $zb_{lim}$ by using the limit movement amount calculator 321 of the control device 300 illustrated in FIG. 8. In FIG. 9, elements similar to those illustrated in FIGS. 6A to 6D are denoted by the same numerals, and detailed description thereof will be omitted.

First, the limit movement amount calculator 321 assumes that the electric stage 220 has moved forward to a certain movement amount $zb_0$, and calculates the position of the bending portion 120 at the moment. Next, as shown by a thick dotted line in FIG. 9, the limit movement amount calculator 321 calculates an extension line 910 of the distal end of the bending portion 120 when the bending angle of the bending portion 120 is the maximum bending angle $\theta_{lim}$. Then, the limit movement amount calculator 321 determines that it is possible to sample a tissue of the affected area 602 at the movement amount $zb_0$ if the center of the affected area 602 exists on the extension line 910 and the distance d between the distal end position of the bending portion 120 and the position of the affected area 602 is less than or equal to a threshold $r_{th}$, sets the movement amount $zb_0$ at the moment as the maximum movement amount $zb_{lim}$, and outputs the maximum movement amount $zb_{lim}$. On the other hand, the limit movement amount calculator 321 determines that it is difficult to sample a tissue of the affected area 602 if the center of the affected area 602 does not exist on the extension line 910 or, even if the center exists there, if the distance d is greater than the threshold $r_{th}$. Then, the limit movement amount calculator 321 calculates a new movement amount by adding a very small positive amount to the movement amount $zb_0$, and repeats the calculation described above until the maximum movement amount $zb_{lim}$ is found.

The control device 300 of the continuum robot control system 10-2 according to the second embodiment performs the following process.

To be specific, the control device 300 calculates the maximum movement amount $zb_{lim}$ of the continuum robot 100 due to the electric stage 220, which is a movement device, based on the position (the affected area position 304) of the affected area 602, which is the region of interest of a test subject, the target path (the target path 307) of the bending portion 120 to the position of the affected area 602, and the maximum bending angle $\theta_{lim}$. Then, the control device 300 controls the electric stage 220 so that the continuum robot 100 moves within the range of the calculated maximum movement amount $zb_{lim}$.

With such a configuration, it is possible to increase the success rate of sampling a tissue from the affected area 602, because the tissue can be sampled from the affected area 602 after positioning the distal end of the bending portion 120 sufficiently close to the affected area 602.

Third Embodiment

Next, a third embodiment of the present invention will be described. In the following description of the third embodiment, description of matters common to those of the first and second embodiments described above will be omitted, and matters different from those of the first and second embodiments described above will be described.

A continuum robot control system 10 according to the third embodiment can have a configuration similar to that of the continuum robot control system 10-1 according to the first embodiment illustrated in FIG. 1 or that of the continuum robot control system 10-2 according to the second embodiment illustrated in FIG. 7.

As described above in the first embodiment, the elongated portion 110 of the continuum robot 100 can bend passively when contacting the lumen 601 inside of a test subject. However, since it is not possible to actively control the posture of the elongated portion 110, for example, when pushed into a path in the lumen 601 that is bent at a large angle, the elongated portion 110 bends at an angle greater than the maximum bending angle $\theta_{lim}$. Then, in this case, it becomes difficult to insert a tool through the tool channel 101 of the continuum robot 100. Thus, in the third embodiment, a continuum robot 100 including a plurality of bending portions 120 is used, and the bending angle is controlled so that all bending portions 120 have angles less than or equal to the maximum bending angle $\theta_{lim}$ when the distal end of a bending portion located at the distal end reaches the vicinity of the affected area 602.

3-1. Configuration of Continuum Robot

Figure 10:
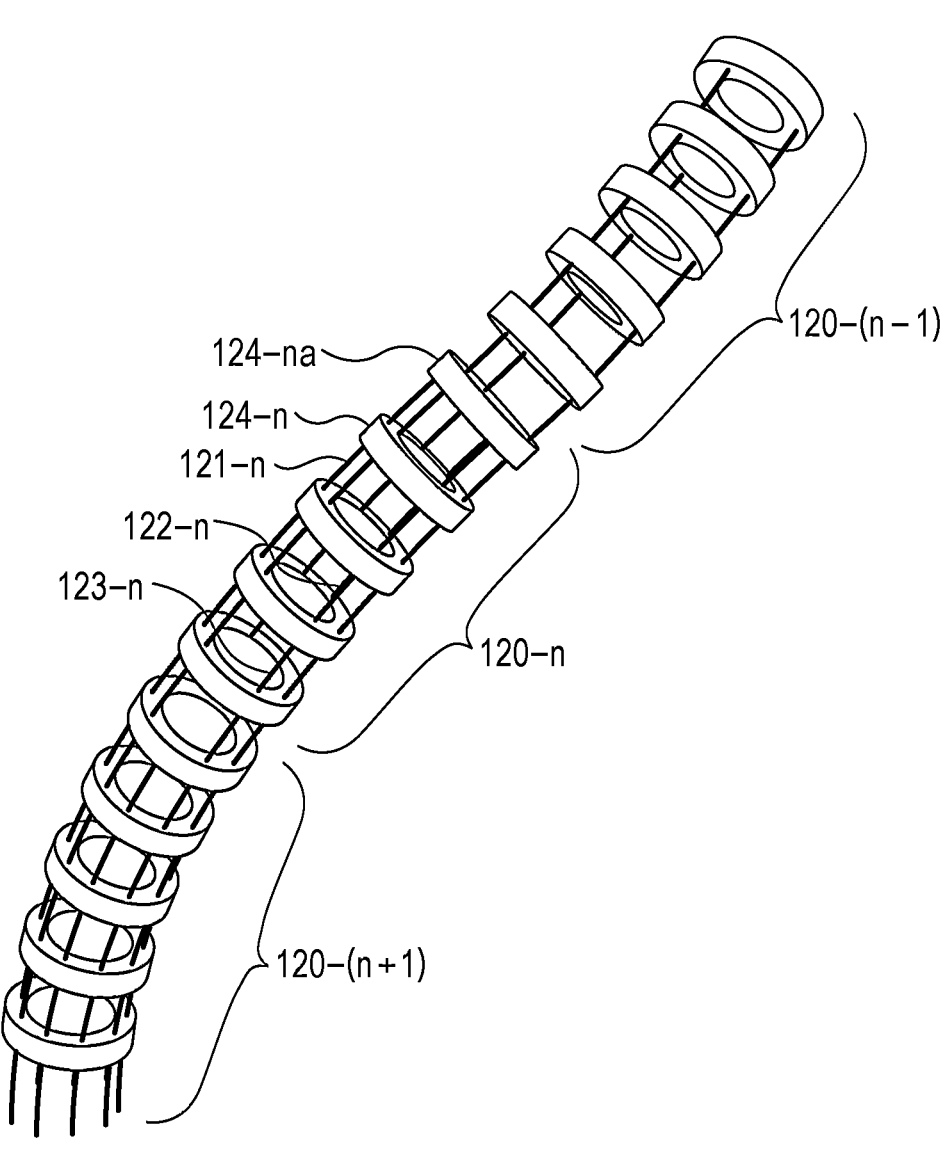
FIG. 10 is a schematic view illustrating an example of a plurality of bending portions of a continuum robot according to a third embodiment of the present invention.

FIG. 10 is a schematic view illustrating an example of the plurality of bending portions 120 of the continuum robot 100 according to the third embodiment of the present invention. In FIG. 10, elements similar to those illustrated in FIG. 2 are denoted by the same numerals and detailed description thereof will be omitted.

In the present embodiment, the number of the bending portions 120 is N. In FIG. 10, among the N bending portions 120, a certain bending portion 120 is illustrated as the n-th bending portion 120-n. In the n-th bending portion 120-n, one end of each of drive wires 121-n, 122-n, and 123-n is fixed and connected to a wire guide 124-na that is located at the distal end among a plurality of wire guides 124-n. To be specific, FIG. 10 illustrates three bending portion 120 in order from the distal end of the continuum robot 100, which are the (n−1)-th bending portion 120-(n−1), the n-th bending portion 120-n, and the (n+1)-th bending portion 120-(n+1).

The drive wires 121-n, 122-n, and 123-n of the n-th bending portion 120-n are guided by the wire guide of the (n+1)-th the bending portion 120-(n+1) and the elongated portion 110, and connected to an actuator (not shown). Then, it is possible to control the bending angle θn and the bending direction of the n-th bending portion 120-n by driving the actuator.

3-2. Configuration of Control Device

With the control device 300 according to the first embodiment, a user controls the posture of the bending portion 120 along the shape the lumen 601 by using the operation device 500. However, with the continuum robot 100 according to the present embodiment, which includes the plurality of bending portions 120, a complex operation is necessary to control the postures of all bending portions 120 along the shape of the lumen 601, and usability decreases. Thus, leader following control, with which it is possible to control the posture of the continuum robot 100 along a bent path in the lumen 601 with a simple operation, is used. Here, first, the leader following control according to the present embodiment will be described, and next, a method of applying a bending angle limitation according to the present invention to the control device 300 that performs the leader following control will be described.

In the leader following control according to the present embodiment, a user operates only the posture of a first bending portion corresponding to the (n−1)-th bending portion 120-(n−1) located at the distal end of the continuum robot 100 in FIG. 10. That is, the first bending portion is a bending portion that serves as a leader when the continuum robot 100 moves forward relative to a test subject. Then, in the present embodiment, the control device 300 controls the postures of the second bending portion, corresponding to the n-th bending portion 120-n illustrated in FIG. 10, to the N-th bending portions (if N=3, the (n+1)-th bending portion 120-(n+1) illustrated in FIG. 10) in such a way as to follow the posture of the first bending portion. Here, the second bending portion is a bending portion that moves forward in such a way as to follow the first bending portion when the continuum robot 100 moves forward relative to a test subject.

To be specific, for example, as with the continuum robot control system 10-1 according to the first embodiment, a user operates the posture of the first bending portion along the shape of the lumen 601 while referring to the camera image 610 and the navigation image 620 displayed on the image display device 600. Then, the user moves the stage forward after determining the bending angle of the first bending portion. The user repeats this operation to cause the distal end of the first bending portion to reach the affected area 602.

At this time, the control device 300 controls the postures of the second to N-th bending portions that move forward in such a way as to follow the first bending portion when moving forward so as to coincide with the bending angle of the first bending portion operated by the user. At this time, first, each time the movement amount $z_b$ of the stage changes, the control device 300 stores the target bending angle $\theta1_{ref}(z_b)$ of the first bending portion corresponding to the movement amount $z_b$ of the stage in an internal storage (not shown). Then, when a bending portion that follows the first bending portion when moving forward reaches a position at a certain entry depth inside of a test subject, the control device 300 reads out from the storage a target bending angle when the first bending portion passed the position, and sets this as a target bending angle of the bending portion that follows. For example, when the stage is moved forward by the length L1 of the first bending portion, the movement amount of the second bending portion becomes the same as that of the first bending portion before the movement. Accordingly, a target bending angle $\theta2_{ref}$ of the second bending portion is represented by the following expression (1).

$$\theta2_{ref} = \theta1_{ref}(zb - L_1) \tag{1}$$

Moreover, when the stage is moved further by the length L2 of the second bending portion, since the movement amount of the third bending portion reaches a movement amount that is the same as that of the first bending portion before the movement, the target bending angle $\theta 3_{ref}$ of the third bending portion is represented by the following expression (2).

$$\theta 3_{ref} = \theta 1_{ref}(zb - L_1 - L_2) \qquad (2)$$

By similar calculations, in general, the target bending angle $\theta n_{ref}$ of the n-th bending portion is represented by the following expression (3).

$$\theta n_{ref} = \theta_{ref}\left(zb - \sum_{i=1}^{n-1} L_i\right) \qquad (3)$$

Then, the control device 300 controls the wire driving amount, which is the amount by which the drive wire is pushed and pulled, so that the bending angle of each bending portion coincides with the target bending angle $\theta n_{ref}$. Thus, when the user controls the posture of the first bending portion along the shape of the lumen 601, the second bending portion and the subsequent bending portions that follow can enter the lumen 601 along the shape of the lumen 601.

However, with the leader following control, since the bending angle of the first bending portion is transmitted to the bending angle of bending portions that follow, if the first bending portion is bent at a large angle when proceeding in the lumen 601, the bending portions that follow also bend at a large angle. In this case, it is not possible to insert a tool when reaching the vicinity of the affected area 602. Thus, the control device 300 according to the present embodiment estimates beforehand the position $P_n$ of the distal end of the n-th bending portion when the first bending portion reaches the affected area 602 based on the target path 307 to the affected area 602. Then, the control device 300 according to the present embodiment limits the target bending angle $\theta 1_{ref}$ within the range of the maximum bending angle $\theta_{lim}$ (less than or equal to the maximum bending angle $\theta_{lim}$) when the first bending portion passes the vicinity of the position $P_n$ during surgery. Thus, when the first bending portion actually reaches the vicinity of the affected area 602, it is possible to cause the bending angle of the n-th bending portion $\theta n_{ref}$ located in the vicinity of the position $P_n$ to be within the range of the maximum bending angle $\theta_{lim}$ (less than or equal to the maximum bending angle $\theta_{lim}$).

Figure 11:
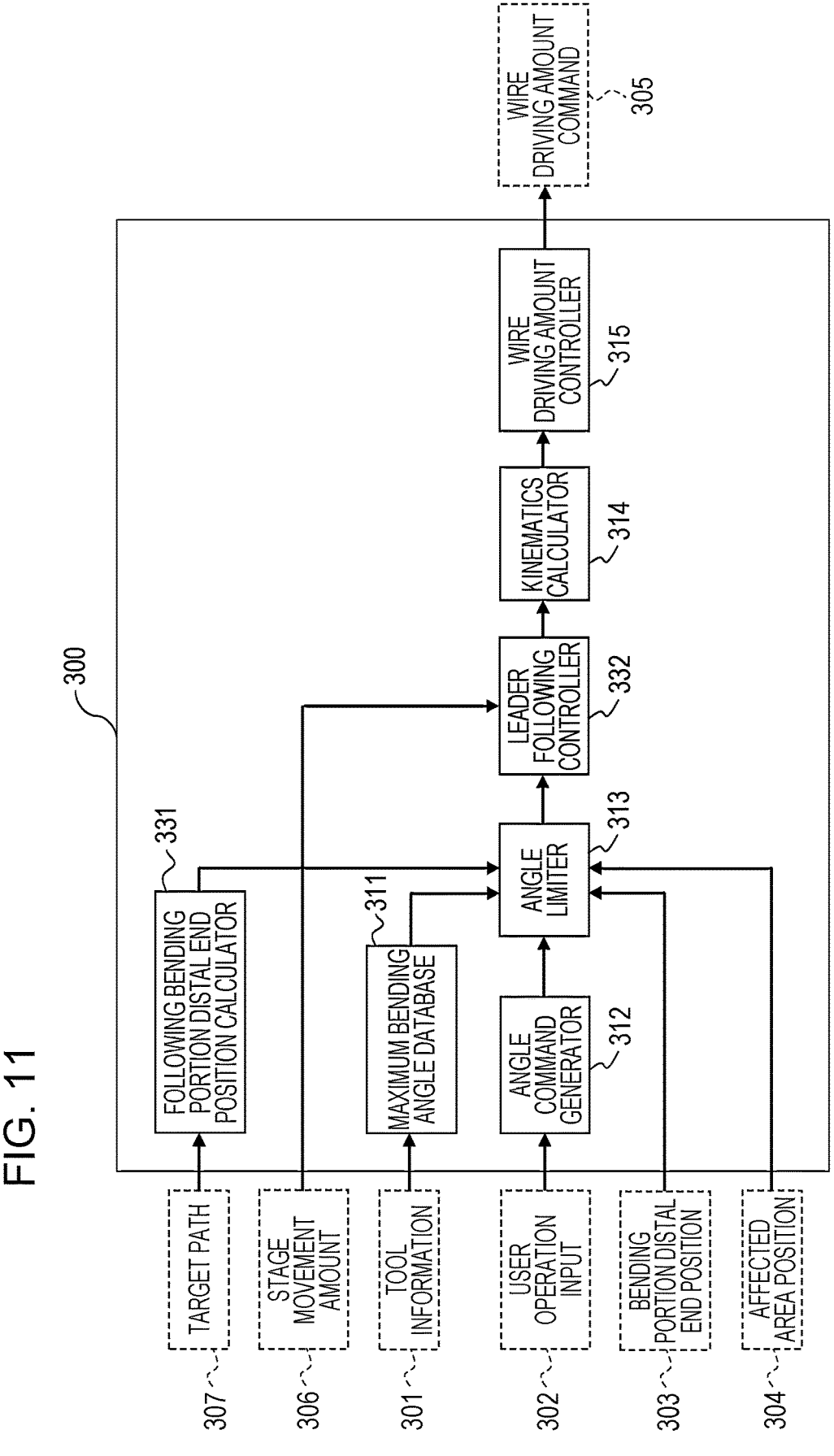
FIG. 11 is a schematic view illustrating an example of a schematic configuration of a control device according to the third embodiment of the present invention.

FIG. 11 is a schematic view illustrating an example of a schematic configuration of the control device 300 according to the third embodiment of the present invention. In FIG. 11, elements similar to those illustrated in FIGS. 4 and 8 are denoted by the same numerals, and detailed description thereof will be omitted.

The control device 300 illustrated in FIG. 11 includes the maximum bending angle database 311, the angle command generator 312, the angle limiter 313, the kinematics calculator 314, the wire driving amount controller 315, a following bending portion distal end position calculator 331, and a leader following controller 332. That is, the control device 300 illustrated in FIG. 11 has a configuration such that the following bending portion distal end position calculator 331 and the leader following controller 332 are added to the control device 300 according to the first embodiment illustrated in FIG. 4. Note that, in the present invention, it is also possible to use a configuration such that the following bending portion distal end position calculator 331 and the leader following controller 332 illustrated in FIG. 11 are added to the control device 300 according to the second embodiment illustrated in FIG. 8.

The following bending portion distal end position calculator 331 is an element that determines a condition of limiting the bending angle. The following bending portion distal end position calculator 331 calculates and outputs the position $P_n$ of the distal end of a following bending portion (the second bending portion or a subsequent bending portion) when the first bending portion reaches the affected area 602 based on the inputted target path 307 and the length of each bending portion.

The angle limiter 313 limits the target bending angle $\theta 1_{ref}$ of the first bending portion to be less than or equal to the maximum bending angle $\theta_{lim}$ when the distance between the present position P of the distal end of the first bending portion and the position $P_n$ calculated by the following bending portion distal end position calculator 331 is less than equal to a certain value.

Based on an output of the angle limiter 313, the leader following controller 332 controls the posture of each bending portion so that the second bending portion and the subsequent following bending portions follow the first bending portion.

Figure 12:
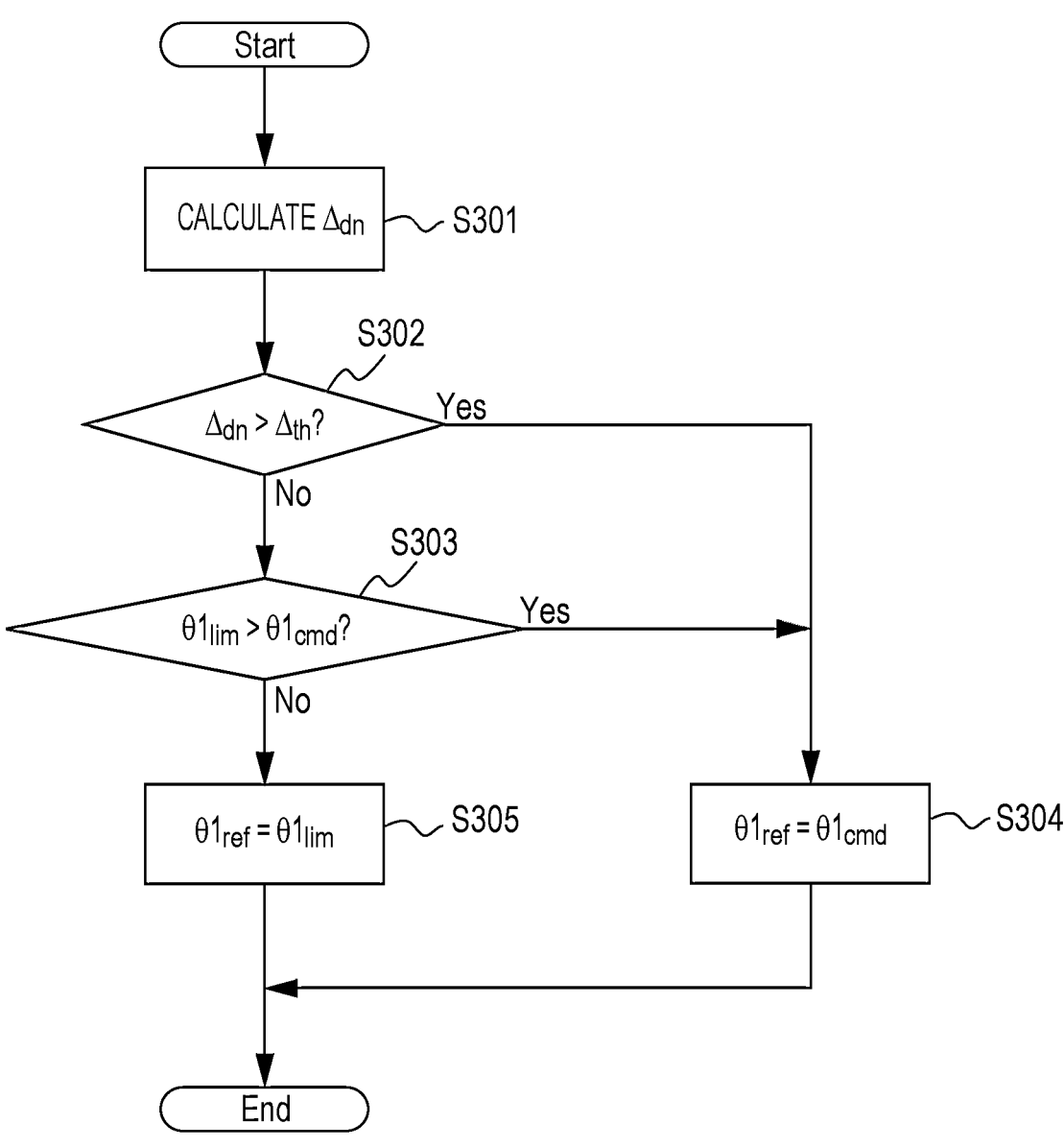
FIG. 12 is a flowchart illustrating an example of a process performed by an angle limiter of the control device illustrated in FIG. 11.

FIG. 12 is a flowchart illustrating an example of a process performed by the angle limiter 313 of the control device 300 illustrated in FIG. 11.

To be specific, first, in step S301 of FIG. 12, the angle limiter 313 calculates the distance $\Delta_{dn}$ between the present position P of the distal end of the first bending portion and the position $P_n$ calculated by the following bending portion distal end position calculator 331.

Next, in step S302, the angle limiter 313 determines whether or not the distance $\Delta_{dn}$ calculated in step S301 is greater than the threshold $\Delta_{th}$.

If it is determined in step S302 that the distance $\Delta_{dn}$ calculated in step S301 is not greater than the threshold $\Delta_{th}$ (the distance $\Delta_{dn}$ is less than or equal to the threshold $\Delta_{th}$) (S302/No), the process proceeds to step S303.

In step S303, the angle limiter 313 determines whether or not the maximum bending angle $\theta 1_{lim}$ of the first bending portion outputted from the maximum bending angle database 311 is greater than the bending angle command value $\theta 1_{cmd}$ of the first bending portion generated by the angle command generator 312.

If it is determined in step S303 that the maximum bending angle $\theta 1_{lim}$ is greater than the bending angle command value $\theta 1_{cmd}$ (S303/Yes) or if it is determined in step S302 that the distance $\Delta_{dn}$ is greater than the threshold $\Delta_{th}$ (S302/Yes), the process proceeds to step S304.

In step S304, the angle limiter 313 sets the bending angle command value $\theta 1_{cmd}$ generated by the angle command generator 312 as the target bending angle $\theta 1_{ref}$ of the bending portion 120, and outputs the target bending angle $\theta 1_{ref}$.

On the other hand, if it is determined in step S303 that the maximum bending angle $\theta 1_{lim}$ is not greater than the bending angle command value $\theta 1_{cmd}$ (the maximum bending angle $\theta 1_{lim}$ is less than or equal to the bending angle command value $\theta 1_{cmd}$) (S303/No), the process proceeds to step S305.

In step S305, the angle limiter 313 sets the maximum bending angle $\theta 1_{lim}$ outputted from the maximum bending angle database 311 as the target bending angle $\theta 1_{ref}$ of the bending portion 120, and outputs the target bending angle $\theta 1_{ref}$.

When the processing in step S304 has finished or the processing in step S305 has finished, the process of the flowchart of FIG. 12 finishes.

In this way, by performing the leader following control while limiting the bending angle, it is possible to insert the continuum robot 100 including the plurality of bending portions 120 into the lumen 601 of a test subject while controlling the posture so as to enable insertion and extraction of a tool.

In the present embodiment, an example in which the maximum bending angles of all bending portions 120, including the first bending portion, are limited to be less than or equal to the maximum bending angle $\theta_{lim}$ (the maximum bending angle $01_{lim}$) when the continuum robot 100 reaches the affected area 602 has been described. This is because, in order to sample a tissue (specimen) of the affected area 602 by using a biopsy tool such as the biopsy brush tool 720 or the biopsy needle tool 730 described in the first embodiment, it is necessary that all bending portions 120 of the continuum robot 100 allow high-rigidity members of these tools to pass therethrough. However, when a tool whose distal end portion is constituted by a low-rigidity member and in which a high-rigidity member is located on the driving unit 150 side is to be used, it is not necessary to set a limit on the bending angle of a bending portion 120 that need not allow the high-rigidity member to pass. For example, if it is possible to sample a tissue of the affected area 602 by inserting a tool up to the second bending portion, the target bending angle $\theta n_{ref}$ of the n-th bending portion may be constantly the bending angle command value $\theta n_{cmd}$ that a user indicates. In this way, it is possible to improve usability by limiting the bending angles of only the bending portions 120 that are necessary for insertion/extraction of a biopsy tool.

The control device 300 of the continuum robot control system 10 according to the third embodiment performs the following process.

To be specific, if the control device 300 has controlled the actuator in the driving unit 150, which is a driving portion, so that the first bending portion bends within the range of the maximum bending angle $\theta_{lim}$ (the maximum bending angle $01_{lim}$) when the first bending portion reaches a predetermined position, the control device 300 controls the actuator in the driving unit 150 so that the second bending portion bends within the range of the maximum bending angle $\theta_{lim}$ (the maximum bending angle $01_{lim}$) when the second bending portion reaches the predetermined position described above.

With such a configuration, in addition the advantageous effects of the first embodiment, it is possible to avoid a trouble in that a tool cannot be inserted through the tool channel 101 when the distal end of the continuum robot 100 reaches the vicinity of the affected area 602.

Other Embodiments

In the first to third embodiments described above, examples in which an object into which the bending portion 120 of the continuum robot 100 is to be inserted is a test subject, such as a patient, have been described. However, the present invention is not limited to this. An object into which the bending portion 120 of the continuum robot 100 is to be inserted may be another test body such as a pipe.

The present invention can also be realized as a process of supplying a program that realizes one or more functions of the embodiments described above to a system or an apparatus via a network or a storage medium and causing one or more processors of a computer of the system or the apparatus to read and execute the program. The present invention can also be realized as a circuit (such as an ASIC) that realizes one or more functions.

This program and a computer-readable storage medium storing the program are included in the present invention.

With the present invention, it is possible to reduce time and effort required for a manipulation when the manipulation is performed to insert and extract a plurality of different tools into and from a tool channel after a bending portion of a continuum robot has been inserted to the inside of a test body.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A continuum robot control system comprising:
a continuum robot including:
a bending portion that bends with respect to a reference axis when a linear member is driven,
a driving portion that drives the linear member, and
a tool channel that is a tubular path extending through an inside of the bending portion and through which a tool is to be inserted and extracted; and
a control device that controls movement of the continuum robot,
wherein the control device is configured to:
acquire tool information identifying a plurality of different tools to be inserted into and extracted from the tool channel,
acquire, from a memory, a plurality of tool-specific maximum values of bending angle, each of the plurality of tool-specific maximum values of bending angle being associated with a respective one of the plurality of different tools identified by the tool information,
set a smallest of the plurality of tool-specific maximum values of bending angle as a maximum bending angle of the continuum robot, and
control the driving portion so that the bending portion bends within a range of the maximum bending angle of the continuum robot.

2. The continuum robot control system according to claim 1, wherein, if a distance between a distal end position of the bending portion and a position of a region of interest of a test body is less than or equal to a threshold, the control device controls the driving portion so that the bending portion bends within the range of the maximum bending angle.

3. The continuum robot control system according to claim 1, wherein, if a bending angle command value of the bending portion based on an operation input of a user is less than the maximum bending angle, the control device controls the driving portion by using the bending angle command value as a target bending angle of the bending portion, and, if the bending angle command value is greater than or equal to the maximum bending angle, the control device controls the driving portion by using the maximum bending angle as the target bending angle of the bending portion.

4. The continuum robot control system according to claim 1, further comprising:
a movement device that moves the continuum robot forward and backward relative to a test body,
wherein the control device calculates a maximum movement amount of the continuum robot due to the movement device based on a position of a region of interest of the test body, a target path of the bending portion to the position of the region of interest, and the maximum bending angle, and controls the movement device so that the continuum robot moves within the range of the maximum movement amount.

5. The continuum robot control system according to claim 1, wherein the continuum robot includes a plurality of the bending portions, wherein the plurality of bending portions include a first bending portion that serves as a leader when the continuum robot moves forward relative to a test body and a second bending portion that moves forward in such a way as to follow the first bending portion when the continuum robot moves forward relative to the test body, and wherein, if the control device has controlled the driving portion so that the first bending portion bends within the range of the maximum bending angle when the first bending portion reaches a predetermined position, the control device controls the driving portion so that the second bending portion bends within the range of the maximum bending angle when the second bending portion reaches the predetermined position.

6. A continuum robot control method using a continuum robot control system including a continuum robot including a bending portion that bends with respect to a reference axis when a linear member is driven, a driving portion that drives the linear member, and a tool channel that is a tubular path extending through an inside of the bending portion and through which a tool is to be inserted and extracted, and a control device that controls movement of the continuum robot, the continuum robot control method comprising:

causing the control device to acquire tool information identifying a plurality of different tools to be inserted into and extracted from the tool channel;

causing the control device to acquire, from a memory, a plurality of tool-specific maximum values of bending angle, each of the plurality of tool-specific maximum values of bending angle being associated with a respective one of the plurality of different tools identified by the tool information;

causing the control device to set a smallest of the plurality of tool-specific maximum values of bending angle as a maximum bending angle of the continuum robot; and causing the control device to control the driving portion so that the bending portion bends within a range of the maximum bending angle of the continuum robot.

7. A non-transitory recording medium storing a program for causing a computer to execute the continuum robot control method according to claim 6.

* * * * *